(12) United States Patent
Kuhara

(10) Patent No.: US 8,781,553 B2
(45) Date of Patent: Jul. 15, 2014

(54) MAGNETIC RESONANCE IMAGING APPARATUS AND CONTROL METHOD THEREOF

(75) Inventor: Shigehide Kuhara, Otawara (JP)

(73) Assignees: Kabushiki Kaisha Toshiba, Minato-Ku, Tokyo (JP); Toshiba Medical Systems Corporation, Otawara-Shi, Tochigi (JP)

( * ) Notice: Subject to any disclaimer, the term of this patent is extended or adjusted under 35 U.S.C. 154(b) by 0 days.

(21) Appl. No.: 13/107,109

(22) Filed: May 13, 2011

(65) Prior Publication Data
US 2011/0218424 A1    Sep. 8, 2011

Related U.S. Application Data

(62) Division of application No. 12/149,587, filed on May 5, 2008.

(30) Foreign Application Priority Data

May 7, 2007   (JP) .................................. 2007-122737
Jan. 29, 2008   (JP) ................................ 2008-018232

(51) Int. Cl.
*A61B 5/05*   (2006.01)
*A61B 5/055*   (2006.01)
*A61B 6/00*   (2006.01)
*A61B 5/00*   (2006.01)

(52) U.S. Cl.
CPC ................. *A61B 5/055* (2013.01); *A61B 6/541* (2013.01); *A61B 5/7207* (2013.01); *A61B 5/7285* (2013.01)
USPC ........... 600/413; 600/410; 324/318; 324/307; 324/309

(58) Field of Classification Search
CPC ...... A61B 5/055; A61B 6/541; A61B 5/7205; A61B 5/7285
USPC .................. 600/413, 410; 324/318, 307, 309
See application file for complete search history.

(56) References Cited

U.S. PATENT DOCUMENTS

| | | | | |
|---|---|---|---|---|
| 4,905,699 A | * | 3/1990 | Sano et al. ..................... | 600/413 |
| 5,382,902 A | * | 1/1995 | Taniguchi et al. ............ | 324/309 |

(Continued)

FOREIGN PATENT DOCUMENTS

| | | |
|---|---|---|
| CN | 1432341 A | 7/2003 |
| CN | 1943510 A | 4/2007 |

(Continued)

OTHER PUBLICATIONS

Carlson et al, "Intermittent Mode CT FLuoroscopy-guided Biopsy of the Lung or Upper Abdomen with Breath-hold Monitoring and Feedback: System Development and Feasibility", Radiology, 2003, 229: 906-912.*

(Continued)

*Primary Examiner* — Nicholas Evoy
(74) *Attorney, Agent, or Firm* — Nixon & Vanderhye PC

(57) ABSTRACT

A magnetic resonance imaging apparatus includes a collection unit that applies a uniform static magnetic field to a subject and also applies a radio-frequency magnetic field and a gradient magnetic field to the subject in accordance with a predetermined pulse sequence to collect a magnetic resonance signal from the subject, an imaging unit that images the subject based on the magnetic resonance signal collected by the collection unit, a detection unit that detects a respiratory level of the subject, an informing unit that informs the subject of whether the detected respiratory level falls within an allowable range, and a unit that controls the collection unit and the imaging unit in such a manner that the magnetic resonance signal for imaging is collected and the subject is imaged based on the thus collected magnetic resonance signal for imaging when the detected respiratory level falls within the allowable range.

14 Claims, 20 Drawing Sheets

(56) References Cited

U.S. PATENT DOCUMENTS

| | | | |
|---|---|---|---|
| 5,545,995 A * | 8/1996 | Schneider et al. | 324/318 |
| 5,842,989 A * | 12/1998 | Zur | 600/410 |
| 6,067,465 A * | 5/2000 | Foo et al. | 600/410 |
| 6,073,041 A * | 6/2000 | Hu et al. | 600/410 |
| 6,185,447 B1 * | 2/2001 | Alley et al. | 600/420 |
| 6,381,486 B1 * | 4/2002 | Mistretta et al. | 600/420 |
| 6,466,017 B1 * | 10/2002 | Ganin et al. | 324/318 |
| 6,587,707 B2 * | 7/2003 | Nehrke et al. | 600/410 |
| 6,631,716 B1 * | 10/2003 | Robinson et al. | 128/204.21 |
| 6,704,593 B2 * | 3/2004 | Stainsby et al. | 600/413 |
| 6,937,696 B1 * | 8/2005 | Mostafavi | 378/95 |
| 6,980,846 B2 * | 12/2005 | Hardy et al. | 600/410 |
| 7,054,675 B2 * | 5/2006 | Ma et al. | 600/410 |
| 7,164,268 B2 * | 1/2007 | Mugler et al. | 324/307 |
| 7,170,289 B2 * | 1/2007 | Kumai et al. | 324/309 |
| 7,254,437 B2 * | 8/2007 | Miyazaki | 600/410 |
| 7,418,288 B2 * | 8/2008 | Haselhoff et al. | 600/413 |
| 7,432,710 B2 * | 10/2008 | Takei et al. | 324/318 |
| 7,561,909 B1 * | 7/2009 | Pai et al. | 600/410 |
| 7,570,050 B2 | 8/2009 | Sugiura | |
| 7,593,558 B2 * | 9/2009 | Boese et al. | 382/128 |
| 7,689,263 B1 * | 3/2010 | Fung et al. | 600/410 |
| 7,693,569 B1 * | 4/2010 | Brittain et al. | 600/413 |
| 7,747,313 B2 * | 6/2010 | Kiefer et al. | 600/428 |
| 7,945,305 B2 * | 5/2011 | Aggarwal et al. | 600/413 |
| 8,143,888 B2 | 3/2012 | Sugiura | |
| 2001/0025139 A1 * | 9/2001 | Pearlman | 600/301 |
| 2002/0063560 A1 * | 5/2002 | Debbins et al. | 324/307 |
| 2003/0036693 A1 * | 2/2003 | Avinash et al. | 600/413 |
| 2003/0160612 A1 * | 8/2003 | Yablonskiy et al. | 324/309 |
| 2004/0051529 A1 * | 3/2004 | Zhu et al. | 324/318 |
| 2004/0059213 A1 * | 3/2004 | Kassai et al. | 600/410 |
| 2004/0145367 A1 * | 7/2004 | Duerk et al. | 324/307 |
| 2004/0254492 A1 * | 12/2004 | Zhang et al. | 600/538 |
| 2005/0001615 A1 * | 1/2005 | Sato | 324/306 |
| 2005/0054910 A1 * | 3/2005 | Tremblay et al. | 600/411 |
| 2005/0197586 A1 * | 9/2005 | Pearlman | 600/509 |
| 2005/0201510 A1 * | 9/2005 | Mostafavi | 378/8 |
| 2005/0215882 A1 * | 9/2005 | Chenevert et al. | 600/410 |
| 2005/0218893 A1 * | 10/2005 | Kumai et al. | 324/309 |
| 2006/0224062 A1 * | 10/2006 | Aggarwal et al. | 600/413 |
| 2006/0253015 A1 * | 11/2006 | Nezafat et al. | 600/410 |
| 2007/0076846 A1 * | 4/2007 | Ruchala et al. | 378/65 |
| 2007/0080690 A1 * | 4/2007 | Takei et al. | 324/318 |
| 2007/0088211 A1 * | 4/2007 | Cheng et al. | 600/410 |
| 2007/0088212 A1 * | 4/2007 | Takei et al. | 600/413 |
| 2007/0159172 A1 | 7/2007 | Sugiura | |
| 2007/0172029 A1 * | 7/2007 | Felmlee et al. | 378/95 |
| 2008/0200800 A1 | 8/2008 | Kuhara et al. | |
| 2008/0281186 A1 | 11/2008 | Kuhara | |
| 2009/0112083 A1 * | 4/2009 | Aulbach et al. | 600/413 |
| 2010/0026295 A1 | 2/2010 | Sugiura | |
| 2010/0094121 A1 | 4/2010 | Kuhara | |
| 2011/0178388 A1 | 7/2011 | Kuhara | |

FOREIGN PATENT DOCUMENTS

| | | |
|---|---|---|
| CN | 1951323 A | 4/2007 |
| JP | 64-034342 | 2/1989 |
| JP | 6-269426 | 9/1994 |
| JP | 2000-41970 | 2/2000 |
| JP | 2000-157507 | 6/2000 |
| JP | 2004-57226 | 2/2004 |
| JP | 2005-40416 | 2/2005 |
| JP | 2005-278919 | 10/2005 |
| JP | 2006-158762 | 6/2006 |
| JP | 2006-314491 | 11/2006 |
| JP | 2007-29250 | 2/2007 |
| JP | 2007-029250 | 2/2007 |
| JP | 2007-185250 | 7/2007 |
| JP | 2007-185300 | 7/2007 |
| JP | 2008-148806 | 7/2008 |
| JP | 2008-302214 | 12/2008 |
| JP | 2009-178264 | 8/2009 |

OTHER PUBLICATIONS

Official Action dated Feb. 5, 2010, with English translation issued in CN 200810095660.7.

Chinese Office Action Dec. 11, 2011, issued in corresponding Chinese Application No. 201010260781.X with English translation.

Japanese Office Action Nov. 27, 2012, with English translation issued in corresponding Japanese Patent Application No. 2008-018232.

Chinese Office Action mailed Apr. 18, 2011, in CN 2009-10206344.7, including English translation.

Office Action mailed Feb. 25, 2014 in JP 2013-121996 and English translation.

Office Action mailed May 13, 2014 in JP 2013-013383 and English translation.

* cited by examiner

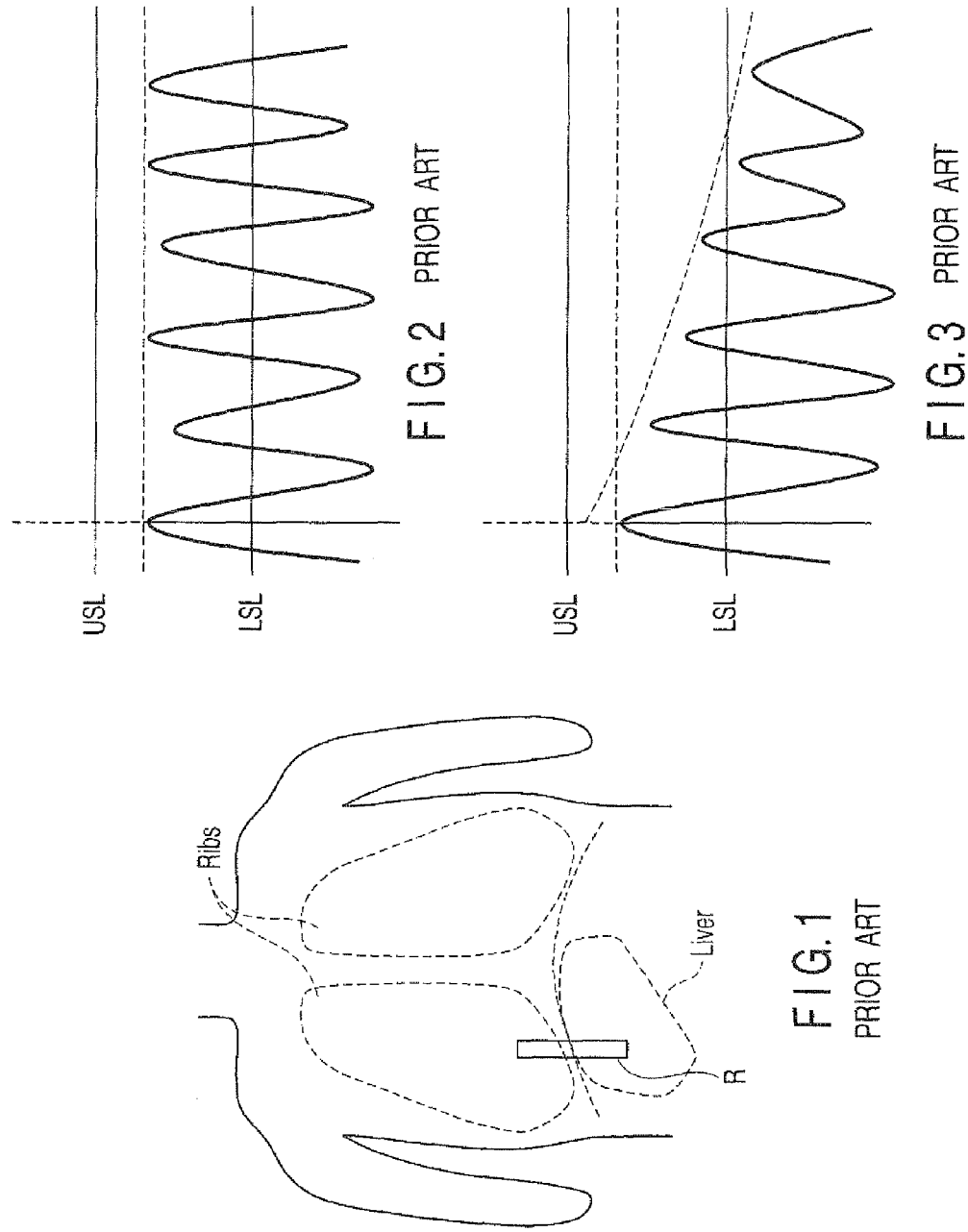

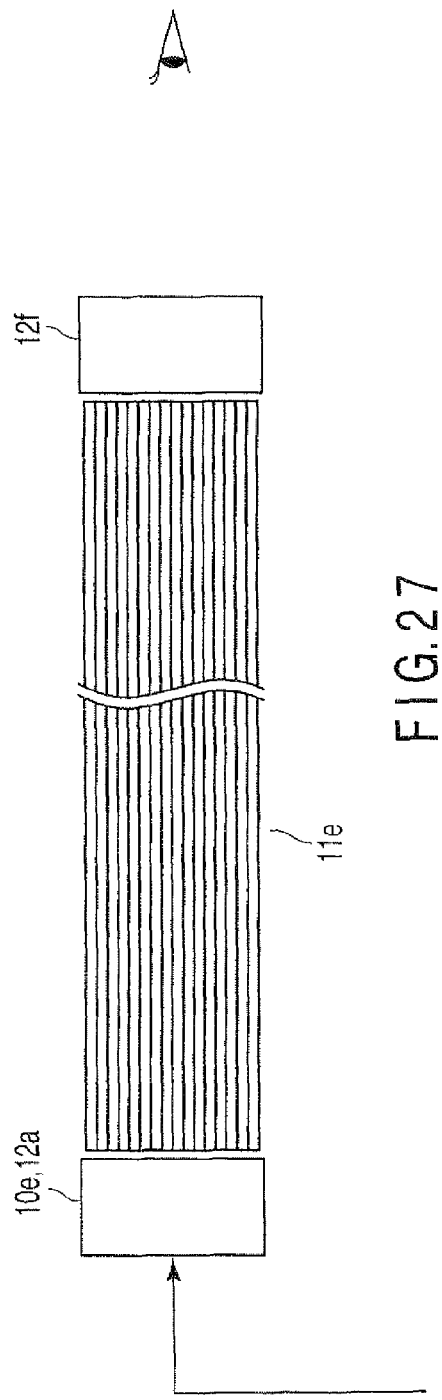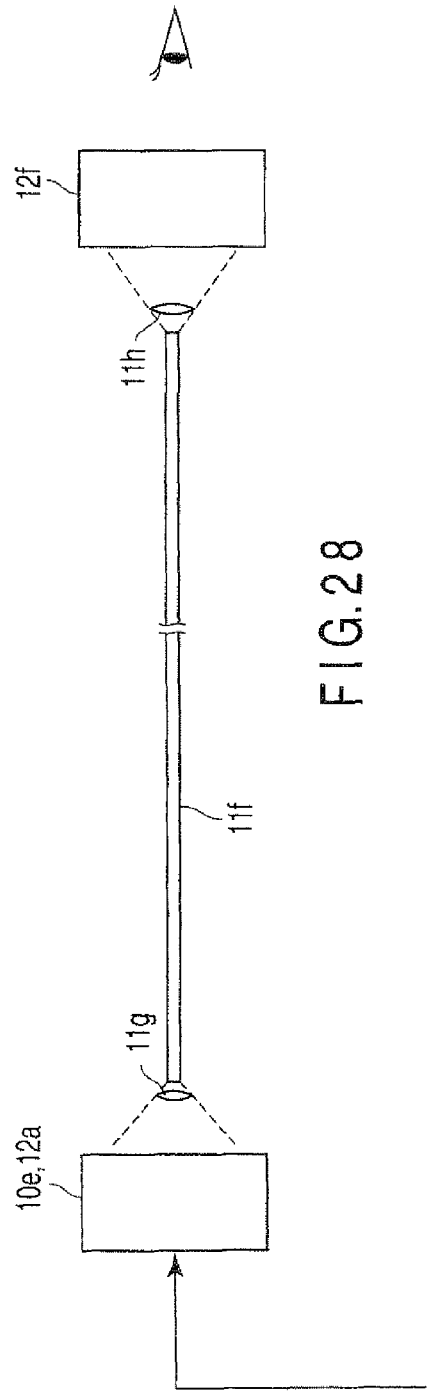

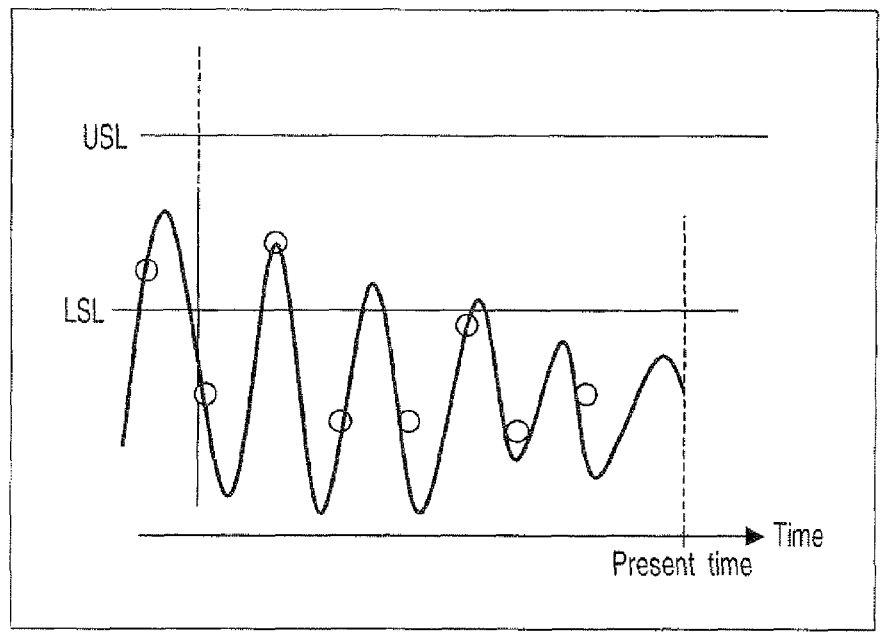
F I G. 3 5
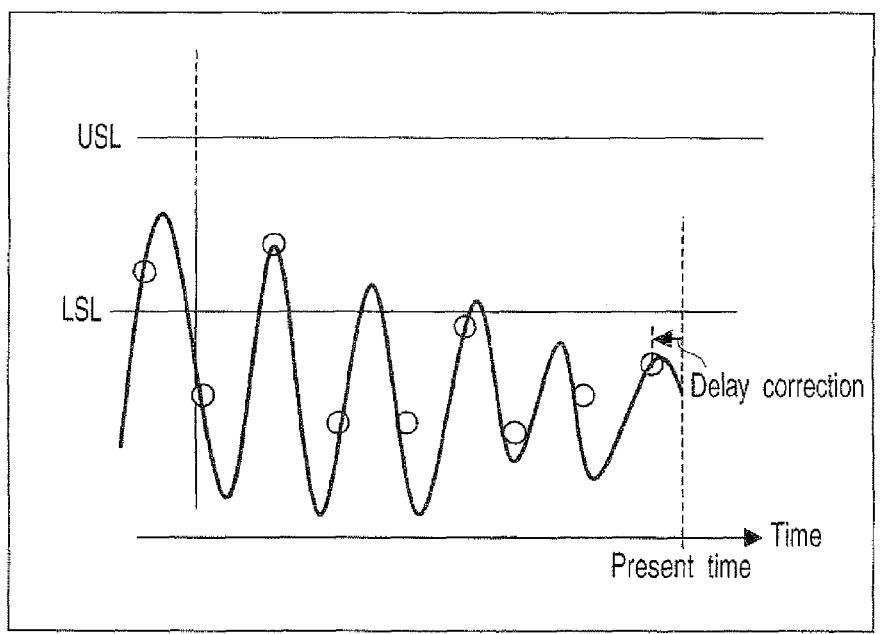
F I G. 3 6

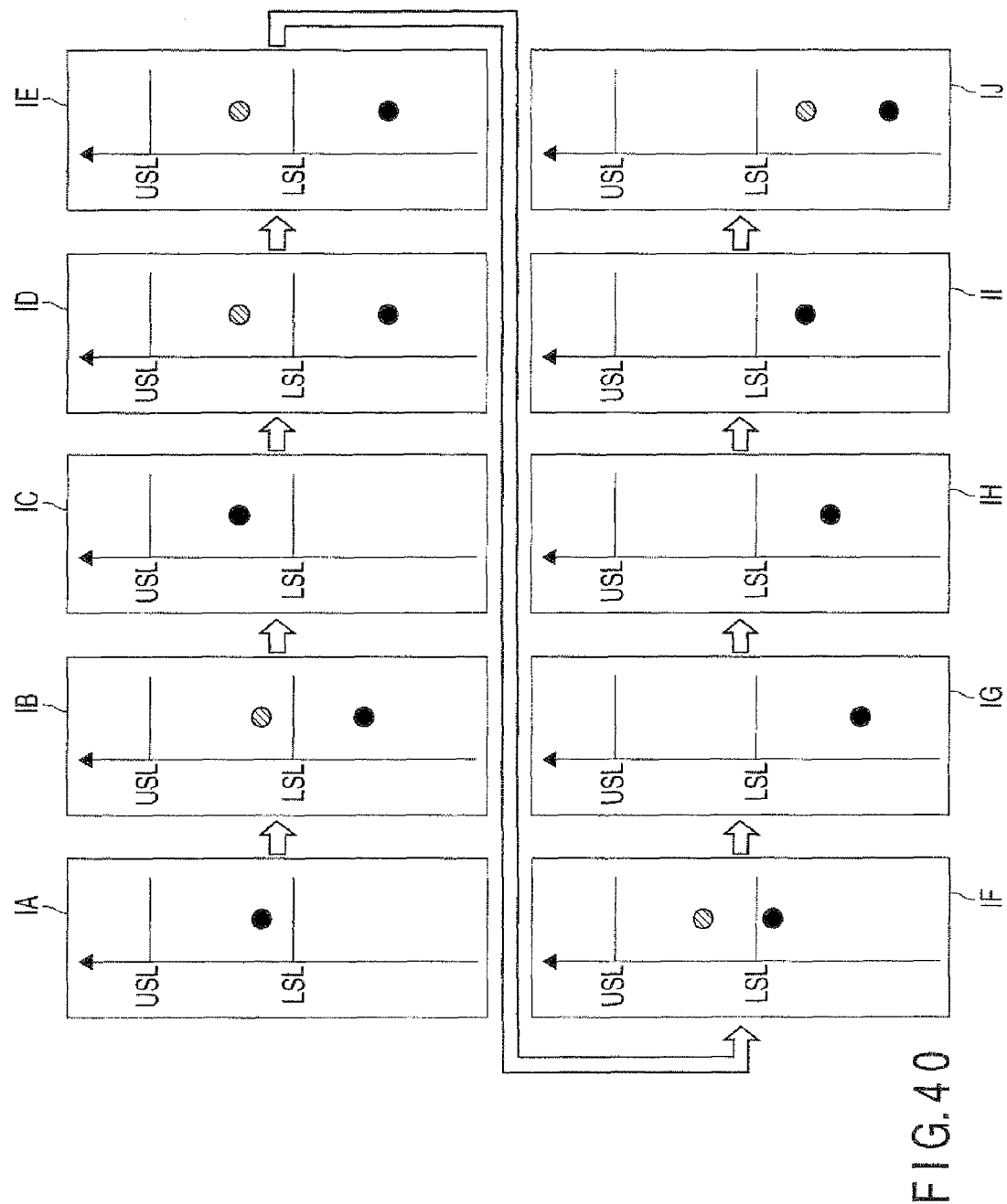
F I G. 40

MAGNETIC RESONANCE IMAGING APPARATUS AND CONTROL METHOD THEREOF

CROSS-REFERENCE TO RELATED APPLICATIONS

This is a division of copending application Ser. No. 12/149,587 filed May 5, 2008, which is based upon and claims the benefit of priority from prior Japanese Patent Applications No. 2007-122737 filed May 7, 2007, and No. 2008-018232 filed Jan. 29, 2008, the entire contents of all of which are incorporated herein by reference.

This application is also related to copending application Ser. No. 12/579,500 filed Oct. 15, 2009, and Ser. No. 13/010,042 filed Jan. 20, 2011.

BACKGROUND

1. Field

The present invention relates to a magnetic resonance imaging apparatus that obtains an image of a subject based on a nuclear magnetic resonance (NMR) signal emitted from the subject, and a control method thereof.

2. Related Art

To image a coronary artery based on the magnetic resonance image (MRI) method, a method of using a three-dimensional (3D) steady-state free precession (SSFP) sequence to perform imaging in a breath-holding state or a voluntary breathing state is used. In case of whole heart MR coronary angiography (WH MRCA) where a course of a coronary artery of an entire heart is imaged in particular, holding a breath may lead to an insufficient spatial resolution in some cases.

As a countermeasure, there is used a real-time motion correction (RMC) method of detecting a position of, e.g., a diaphragm based on an nuclear magnetic resonance (NMR) signal under voluntary breathing to perform imaging while monitoring a respiratory level and changing an imaging position in accordance with this respiratory level.

However, a variable amount of the position that enables accurate imaging is restricted more or less, there is adopted a method of providing a fixed threshold value with respect to a movement range obtained by respiration and pausing collection of the NMR signal for imaging when the movement is large beyond this threshold value. That is, for example, a position of the diaphragm in a body axis direction can be detected from a signal (which will be referred to as a monitor signal) obtained by subjecting an NMR signal collected in relation to such a region R as shown in FIG. 1 to one-dimensional Fourier transformation. Since the position of the diaphragm in the body axis direction cyclically moves up and down in accordance with respiration, plotting the cyclically detected positions of the diaphragm in time-series enables obtaining such a monitor signal as depicted in FIG. 2 that is synchronized with a respiratory motion. When a peak of this monitor signal is out of an allowable range between an upper threshold value USL and a lower threshold value LSL as shown in FIG. 2, imaging is not performed or collected data is not used. When the monitor signal falls within the allowable range, data collection is carried out. Further, imaging is effected while changing an imaging position in accordance with the respiratory motion.

Performing the operation in this manner enables excellently obtaining a 3D image having a resolution that is high even under voluntary breathing.

However, when the respiratory level is not fixed and gradually lowered or gradually increased and a portion of the signal obtained by subjecting the NMR signal to one-dimensional Fourier transformation that corresponds to a position of the diaphragm deviates from the allowable range as shown in, e.g., FIG. 3, an imaging time may become long or, in the worst case, an examination may not be terminated.

Therefore, as shown in, e.g., FIG. 4, a method of using a belt-like fixture, which is a so-called abdominal belt 500, to fix an abdominal is used. This abdominal belt 500 enables obtaining a respiratory motion suppressing effect to some extent.

However, even if the abdominal belt 500 is used to fix the abdominal, the respiratory motion cannot be completely suppressed, and the respiratory level may fluctuate to prolong an examination time in long-time imaging. Furthermore, when fixing strength of the abdominal belt 500 is increased to reduce the respiratory motion, a burden on a subject may be enlarged. When the examination is prolonged, the subject may start moving because of discomfort caused by fixing. Moreover, when the subject has a large body, even the abdominal belt cannot be used.

On the other hand, there is a multi breath-holding method of repeating breath-holding rather than voluntary breathing for a plurality of times to image three-dimensional data.

As shown in FIG. 5, in the multi breath-holding method, collection of data concerning one slab S1 including an entire heart is intermittently performed in synchronization with repetitive breath-holding performed by a subject. In addition, there is a method that additionally uses RMC in the multi breath-holding method and in which collection of data is performed only when a monitor signal is within an allowable range. However, it is difficult for the subject to correctly understand his or her own respiratory level. Even if the subject believes that he/she is uniformly holding breath, the respiratory level fluctuates in breath-holding states. Therefore, when RMC is additionally used, a monitor signal may not fall within an allowable range even though the subject is holding breath, as shown in FIG. 6. In such a case, data is not collected even though the subject is holding breath, which imposes a load on the subject. It should be noted that the inadequate breath-holding state lengthens a period where data cannot be collected, and efficiency for data collection may be lowered, resulting in a long examination time. Additionally, when an imaging time is long, it is often the case that the subject gets tired of having to repeatedly hold his or her breath, the respiratory level in the breath-holding state fluctuates further, and an examination cannot be terminated in the worst case. In the multi breath-holding state that does not additionally use RMC, the data on a number of slabs is acquired in the state of different breath-holding positions. As a result, reconstructed images may be discontinuous at the boundary between the slabs.

On the other hand, as shown in FIG. 7, there is considered a multi-slab method of dividing a region including an entire heart into a plurality of slabs S1 to S4 and individually collecting data from each of slabs S1 to S4. To this case as well, either the simple multi breath-holding method or the multi breath-holding method that additionally uses RMC is applicable. FIG. 8 illustrates the case where the multi breath-holding method that additionally uses RMC is applied, and an allowable range is changed in accordance with each slab. Since in this case the allowable range differs depending upon the slabs, a fault is inevitably produced in each slab if the collected data is used for reconstruction without any correction. A similar fault is produced in the case where the simple multi breath-holding method is applied. The multi-slab method has the following problems. In the case of the multi breath-holding method that additionally uses RMC, the breath-holding positions vary, and the collection of data cannot be performed efficiently, as in the above. In the case of the simple multi breath-holding method, the breath-holding positions vary each time, and blurring of each slab inevitably occurs.

As explained above, according to the voluntary breathing method, a fluctuation in the respiratory level and the long-term variation of the respiratory level degrade an efficiency of data collection based on a navigator echo method.

Further, when a combination of the multi breath-holding method and the single slab method is applied, blurring occurs due to each-time variation of the breath-holding position.

Where the multi breath-holding method and the multi-slab method are applied in combination, the breath-holding position varies each time data is collected from one imaging region. However, the allowable range changes in accordance therewith, data is collected from different positions. Therefore, there is an inconvenience that a registration error is produced in a finally obtained 3D image and discontinuity of data occurs in this 3D image. Thus, to reduce such discontinuity, the respective slabs must be positioned in, e.g., image processing. However, since data positions included in the respective slabs are different from each other during data collection, appropriate positioning is difficult.

It is to be noted that relevant technologies are known from, e.g., JP-A 2000-041970 (KOKAI), JP-A 2000-157507 (KOKAI), or JP-A 2004-057226.

SUMMARY

Under the circumstances, appropriately giving aid so that the subject can readily adapt his/her respiratory level to the allowable range has been demanded.

Further, suppressing occurrence of a registration error or blurring in each slab has been also demanded.

According to a first aspect of the present invention, there is provided a magnetic resonance imaging apparatus comprising: a collection unit that applies a uniform static magnetic field to a subject and also applies a radio-frequency magnetic field and a gradient magnetic field to the subject in accordance with a predetermined pulse sequence to collect a magnetic resonance signal from the subject; an imaging unit that images the subject based on the magnetic resonance signal collected by the collection unit; a detection unit that detects a respiratory level of the subject; an informing unit that informs the subject of whether the detected respiratory level falls within an allowable range; and a unit that controls the collection unit and the imaging unit in such a manner that the magnetic resonance signal for imaging is collected and the subject is imaged based on the thus collected magnetic resonance signal for imaging when the detected respiratory level falls within the allowable range.

According to a second aspect of the present invention, there is provided a magnetic resonance imaging apparatus comprising: a collection unit that applies a uniform static magnetic field to a subject and also applies a radio-frequency magnetic field and a gradient magnetic field to the subject in accordance with a predetermined pulse sequence to individually collect each magnetic resonance signal from the subject in relation to each of a plurality of slabs; an imaging unit that images an imaging region containing the plurality of slabs based on the collected magnetic resonance signals; a unit that detects a respiratory level of the subject; a unit that controls the collection unit to collect the magnetic resonance signal when the detected respiratory level falls within an allowable range that is set with respect to each of the plurality of slabs; and a unit that sets the single allowable range that is applied in common to each of the plurality of slabs based on the respiratory level detected before the collection in relation to the first slab in the plurality of slabs begins.

According to a third aspect of the present invention, there is provided a display apparatus that is used with a magnetic resonance imaging apparatus that visualizes a subject based on a magnetic resonance signal collected from the subject when a respiratory level of the subject falls within an allowable range, comprising: a generation unit that generates an image indicating whether the respiratory level of the subject falls within the allowable range; and a display unit that displays the image to the subject.

According to a fourth aspect of the present invention, there is provided a control method of a magnetic resonance imaging apparatus, the apparatus comprising: a collection unit that applies a uniform static magnetic field to a subject and also applies a radio-frequency magnetic field and a gradient magnetic field to the subject in accordance with a predetermined sequence to collect a magnetic resonance signal from the subject; and an imaging unit that images the subject based on the magnetic resonance signal collected by the collection unit, wherein the method comprises: informing the subject of whether the detected respiratory levels falls within the allowable range; and controlling the collection unit and the imaging unit to collect the magnetic resonance signal and visualize the subject based on the thus collected magnetic resonance signal when the detected respiratory level falls within the allowable range.

According to a fifth aspect of the present invention, there is provided a control method of a magnetic resonance imaging apparatus, the apparatus comprising: a collection unit that applies a uniform static magnetic field to a subject and also applies a radio-frequency magnetic field and a gradient magnetic field to the subject in accordance with a predetermined sequence to individually collect each magnetic resonance signal from the subject in relation to each of a plurality of slabs; and an imaging unit that visualizes an imaging region containing the plurality of slabs based on the collected magnetic resonance signal, wherein the method comprises: detecting a respiratory level of the subject; controlling the collection unit to collect the magnetic resonance signal when the detected respiratory level falls within an allowable range that is set with respect to each of the plurality of slabs; and setting the single allowable range that is applied in common to each of the plurality of slabs based on the respiratory level detected before the collection with respect to the first slab in the plurality of slabs begins.

Additional objects and advantages of the invention will be set forth in the description that follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 1 is a view for explaining a conventional technology;

FIG. 2 is a view for explaining a conventional technology;

FIG. 3 is a view for explaining a conventional technology;

FIG. 27 is a view showing modified structural example of the image transmission system and the display system in FIG. 9;

FIG. 28 is a view showing modified structural examples of the image transmission system and the display system in FIG. 9;

FIG. 35 is a view showing an example of a display image immediately before the first respiratory level is newly detected in the second embodiment;

FIG. 36 is a view showing an example of a display image immediately after the first respiratory level is newly detected in the second embodiment;

FIG. 40 is a view showing an example of a display image generated at each time point in FIG. 39.

DETAILED DESCRIPTION

Embodiments according to the present invention will now be explained hereinafter with reference to the accompanying drawings.

(First Embodiment)

Figure 4:
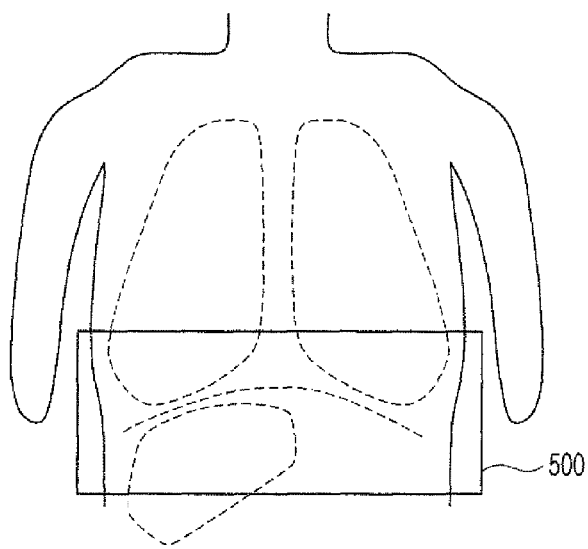
FIG. 4 is a view for explaining a conventional technology.
Figure 5:
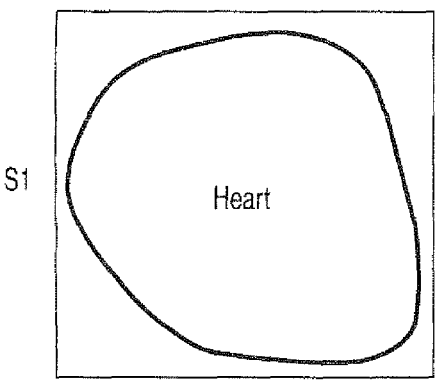
FIG. 5 is a view for explaining a conventional technology.
Figure 6:
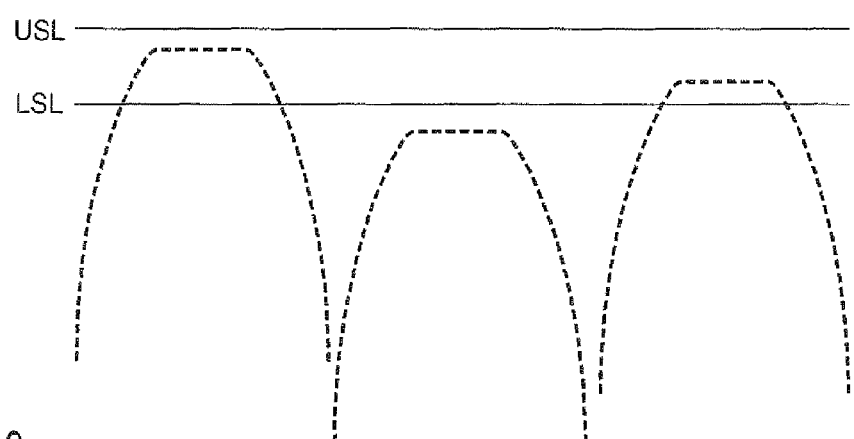
FIG. 6 is a view for explaining a conventional technology.
Figure 7:
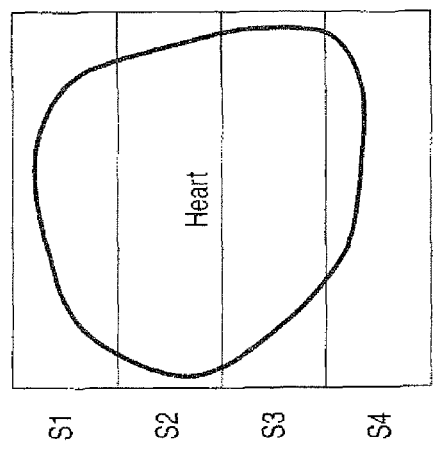
FIG. 7 is a view for explaining a conventional technology.
Figure 8:
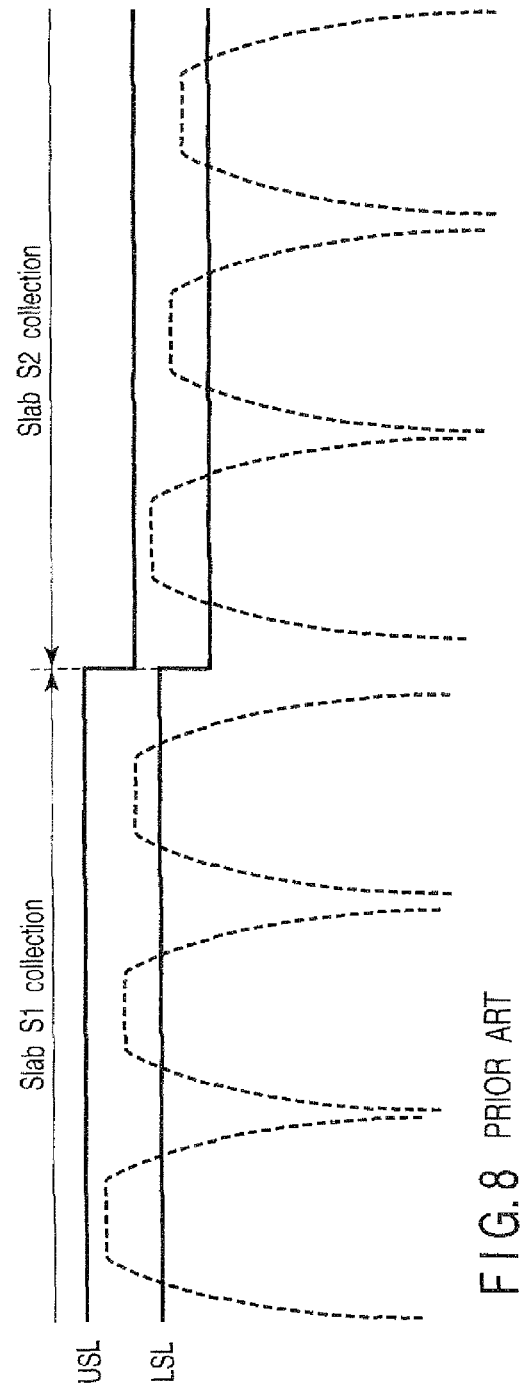
FIG. 8 is a view for explaining a conventional technology.
Figure 9:
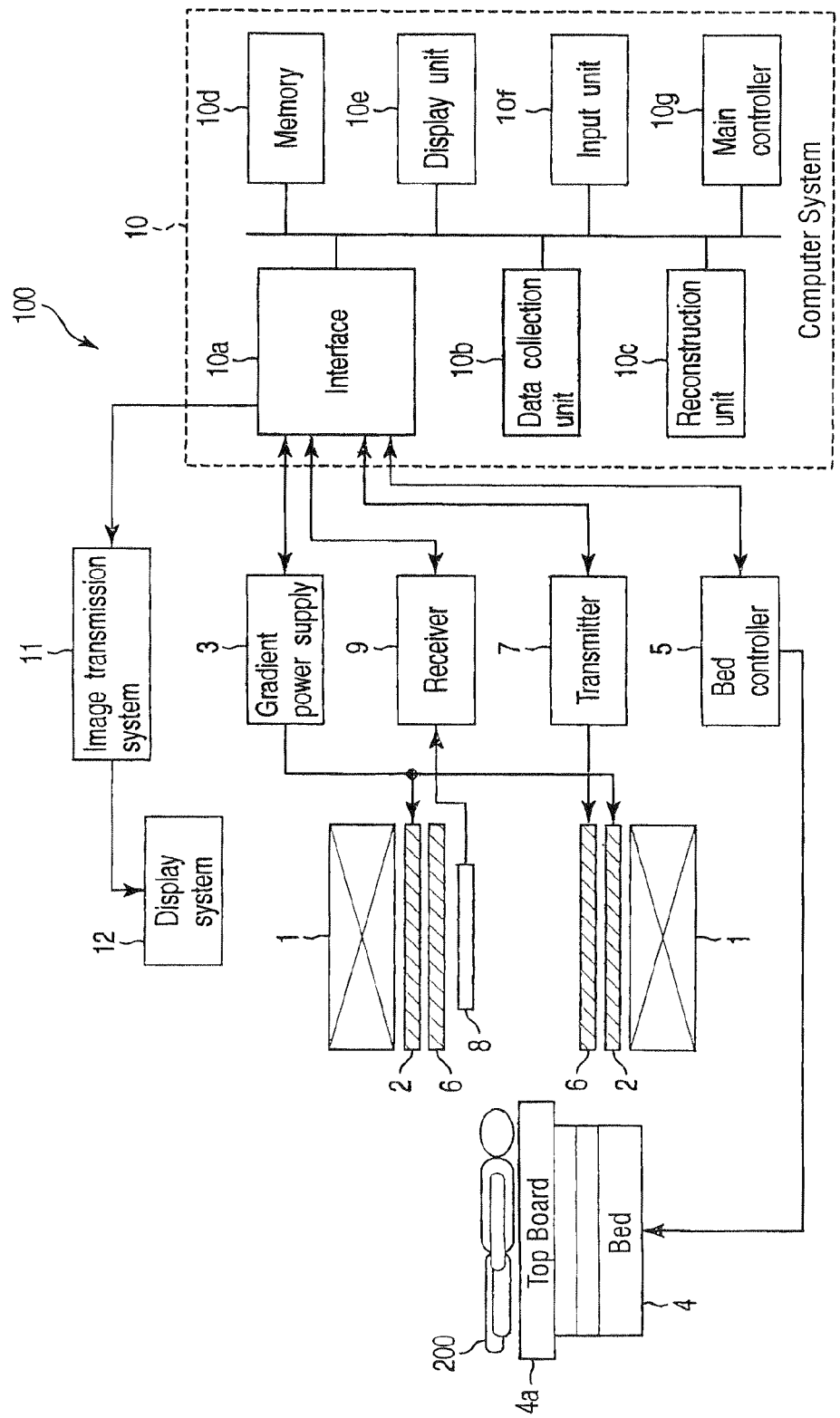
FIG. 9 is a view showing a structure of a magnetic resonance imaging apparatus (an MRI apparatus) according to a first embodiment of the present invention.

FIG. 9 shows the configuration of a magnetic resonance imaging (MRI) apparatus, generally indicated at 100, according to a first embodiment. The MRI apparatus 100 includes a static field magnet 1, a gradient coil 2, a gradient power supply 3, a bed 4, a bed controller 5, a transmission RF coil 6, a transmitter 7, a receiving RF coil 8, a receiver 9, a computer system 10, an image transmission system 11 and a display system 12.

The static field magnet 1 is formed in the shape of a hollow cylinder and adapted to generate a uniform static magnetic field within its inside shape. As the static field magnet 1 use is made of a permanent magnet, a superconducting magnet, or the like.

The gradient coil 2 is formed in the shape of a hollow cylinder and placed inside the static field magnet 1. The gradient coil 2 is a combination of three coils each corresponding to a respective one of the three mutually orthogonal X, Y and Z axes. When the three coils are individually supplied with current from the gradient power supply 3, the gradient coil 2 generates gradient magnetic fields each of which has its strength varied along a corresponding one of the X, Y and Z axes. Suppose that the Z-axis direction coincides with the direction of the static magnetic field. The gradient magnetic fields in the X, Y and Z-axis directions are used as a slice selecting gradient field Gs, a phase encoding gradient magnetic field Ge, and a readout gradient magnetic field Gr, respectively. The slice selecting gradient magnetic field Gs is used to arbitrarily determine an imaging plane section. The phase encoding gradient magnetic field Ge is used to change the phase of NMR signals according to spatial location. The readout gradient magnetic field Gr is used to change the frequency of the NMR signals according to spatial location.

A subject 200 under examination is laid down on a top board 4a of the bed 4 and moved into the space of the gradient coil 2. The top board 4a is driven by the bed controller 5 to move in its lengthwise direction and in an up-and-down direction. Usually, the bed 4 is installed so that its lengthwise direction is parallel to the central axis of the static field magnet 1.

The transmitting RF coil 6 is placed inside the gradient coil 2 and generates a radio-frequency magnetic field in response to application thereto of a radio-frequency pulse from the transmitter 7.

The transmitter 7 has an oscillator, a phase selector, a frequency converter, an amplitude modulator, a radio-frequency power amplifier, etc., built in and transmits radio-frequency pulses corresponding to Larmor frequency to the transmitting RF coil 6.

The receiving RF coil 8 is placed inside the gradient coil 2 and adapted to receive NMR signals emitted from the subject under examination subjected to the radio-frequency magnetic field. The output signal from the receiving RF coil 8 is applied to the receiver 9.

The receiver 9 produces NMR signal data on the basis of the output signal of the receiving RF coil 8.

The computer system 10 includes an interface unit 10a, a data collection unit 10b, a reconstruction unit 10c, a memory unit 10d, a display unit 10e, an input unit 10f, and a main controller 10g.

The interface unit 10a is connected to the gradient power supply 3, the bed controller 5, the transmitter 7, the receiving RF coil 8, and the receiver 9 and allows signals to be transferred between each of these components and the computer system 10.

The data collection unit 10b collects via the interface unit 10a digital signals output from the receiver 9 and then stores the collected digital signals, i.e., the NMR signal data, into the memory unit 10d.

The reconstruction unit 10c performs post-processing, i.e., reconstruction, such as Fourier transforms, on NMR signals data stored in the storage unit 10d to obtain spectrum data of desired nuclear spins within the subject 200 or image data.

The memory unit 10d stores NMR signal data and spectrum data or image data for each subject.

The display unit 10e displays a variety of information, such as spectrum data, image data, etc., under the control of the main controller 10g. As the display unit 10e there is available a display device, such as a liquid crystal display.

The input unit 10f receives a variety of commands and information inputs from an operator. As the input unit 10f there is available a pointing device, such as a mouse or trackball, a selection device, such as a mode changeover switch, or an input device, such as a keyboard. Further, the input unit 10f accepts a specification from the operator of an excitation slice or an excitation slice or an excitation slab including an imaging region of, e.g., an entire heart or a target part such as a diaphragm.

The main controller 10g has a non-illustrated CPU, a memory, and others, and collectively controls the MRI apparatus 100. Furthermore, the main controller 10g generates an image signal of an image indicating whether a respiratory level falls within the allowable range. This image signal is, e.g., an NTSC (national television system committee) signal.

The image transmission system 11 optically transmits the image signal generated by the main controller 10a.

The display system 12 displays an image based on the image signal so that a subject 200 set in an imaging state can visually recognize the image.

Figure 10:
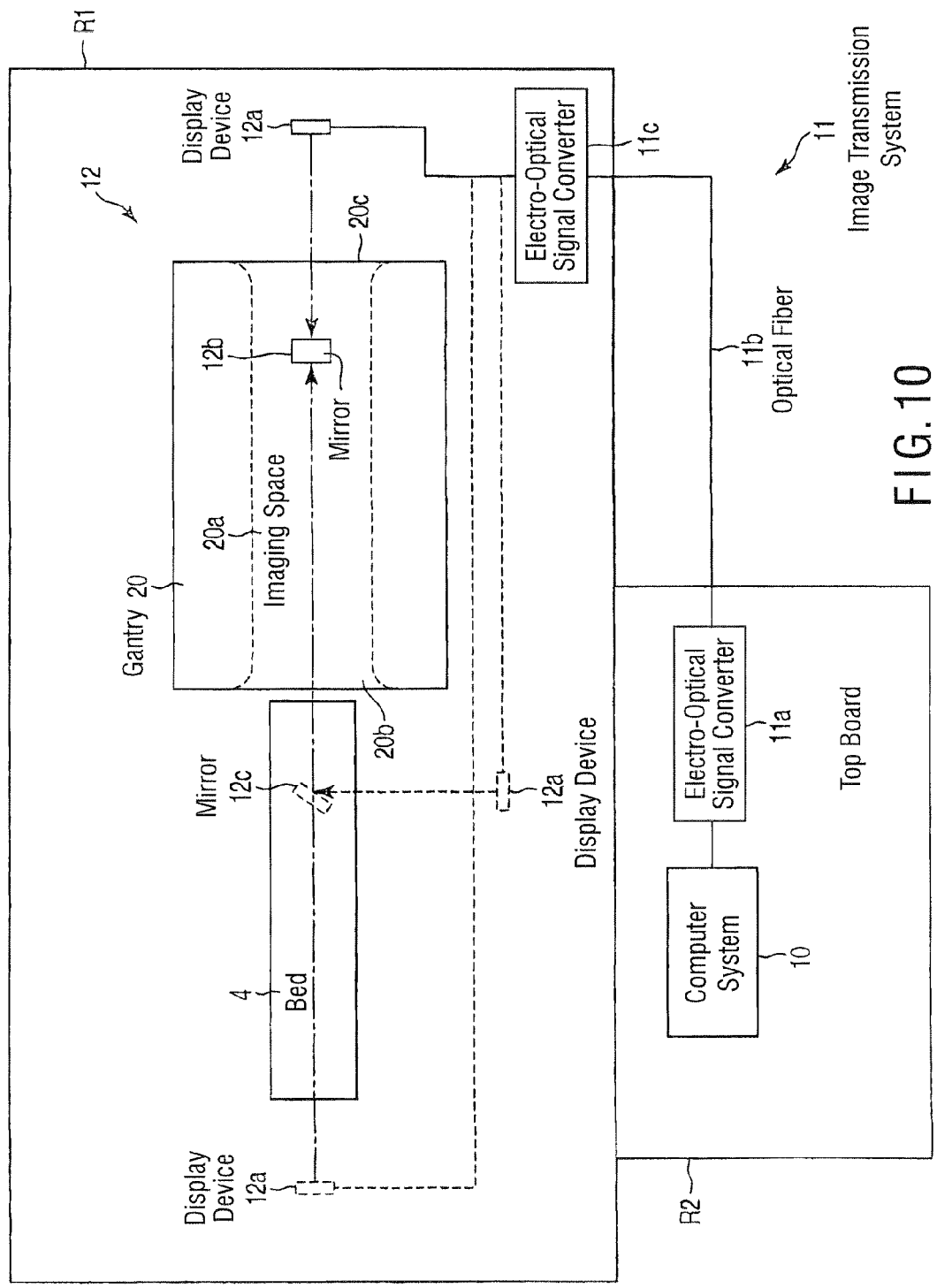
FIG. 10 is a view showing detailed structures of an image transmission system and a display system in FIG. 9.

FIG. 10 is a view showing detailed structures of the image transmission system 11 and the display system 12. It is to be noted that like reference numerals denote parts equal to those in FIG. 9, thereby omitting a detailed explanation thereof.

The image transmission system 11 includes an electric-optical signal converter 11a, an optical cable (an optical fiber cable) 11b, and an optical-electrical signal converter 11c. The display system 12 includes a display device 12a and a mirror 12b.

Reference number 20 in FIG. 10 denotes a gantry. The gantry 20 accommodates the static field magnet 1, the gradient coil unit 2, and the transmission RF coil 6. The gantry 20 has a substantially cylindrical imaging space 20a having a central axis matching with a cylindrical central axis defined by the static field magnet 1 therein, and openings 20b and 20c from which this imaging space 20a is opened to the outside of the gantry 20 are formed at both ends of the imaging space. The bed 4 is arranged on the side of the one opening 20b in close proximity to the gantry 20. Furthermore, the bed 4 supplies the top board 4a from the opening 20b into the imaging space 20a. Therefore, the opening 20b will be referred to as a bed-side opening 20b and the opening 20c will be referred to as a contra-bed-side opening 20c hereinafter.

The gantry 20 and the bed 4 are arranged in a magnetically shielded room R1. The computer system 10 is arranged in an operation room R2 different from the shielded room R1.

The electric-optical signal converter 11a is arranged outside the shielded room R1, i.e., in the operation room R2 in this example. The electric-optical signal converter 11a converts an image signal output as an electrical signal from the interface unit 10a into an optical signal.

The optical cable 11b transmits an image signal output as the optical signal from the electric-optical signal converter 11a to the optical-electric signal converter 11c.

The optical-electric signal converter 11e is arranged in the shielded room R1. The optical-electric signal converter 11e converts an image signal transmitted as the optical signal through the optical cable 11b into an electrical signal.

Thus, the image transmission system 11 transmits the image signal as the optical signal to the shielded room R1.

The display device 12a is arranged in the shielded room R1. The display device 12a displays an image indicated by the image signal output as the electric signal from the optical-electric signal converter 11c. The display device 12a is arranged on the contra-bed-side opening 20c side in a posture that a display plane thereof becomes substantially orthogonal to the central axis of the imaging space 20a and also faces the imaging space 20a. As the display device 12a, a known display device, e.g., a liquid crystal monitor can be utilized. However, the display device 12a includes, e.g., an electromagnetic shield to prevent noise produced therein from leaking into the shielded room R1.

Figure 11:
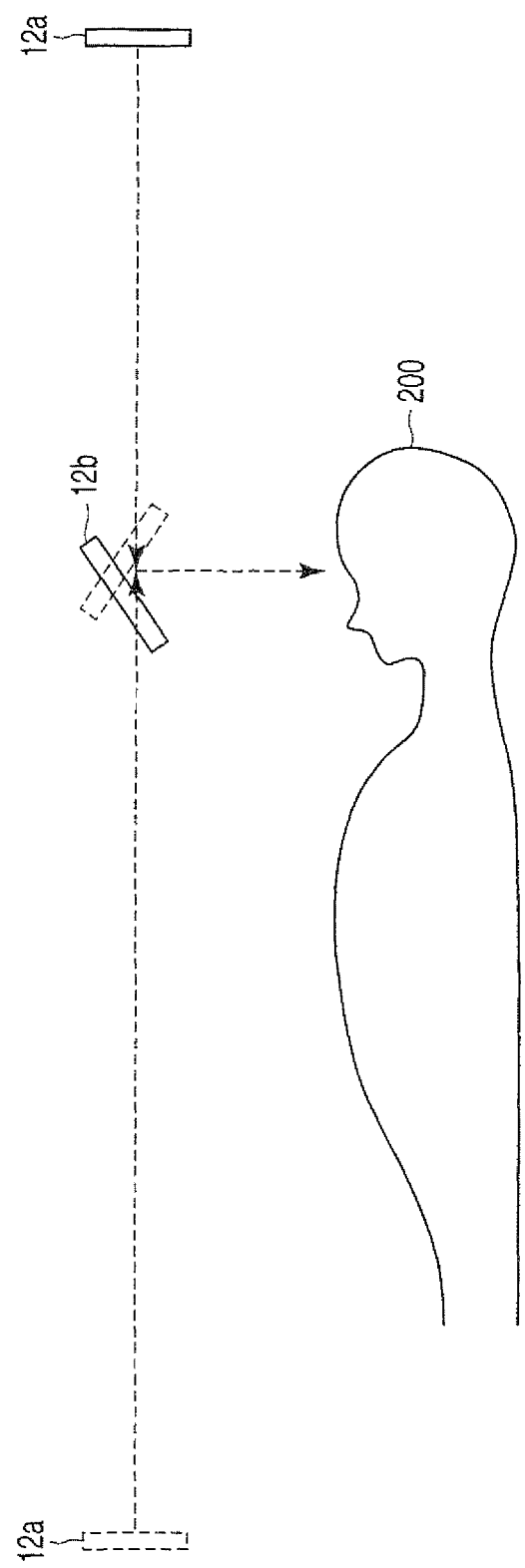
FIG. 11 is a view showing functions of mirrors in FIG. 10.

The mirror 12b is arranged in the imaging space 20a. The mirror 12b reflects an image displayed in the display device 12a as shown in FIG. 11 so that the subject 200 lying down on the top board 4a and carried into the imaging space 20a can visually recognize the image displayed in the display device 12a without changing his/her posture.

An operation of the thus configured MRI apparatus 100 will now be explained.

Figure 12:
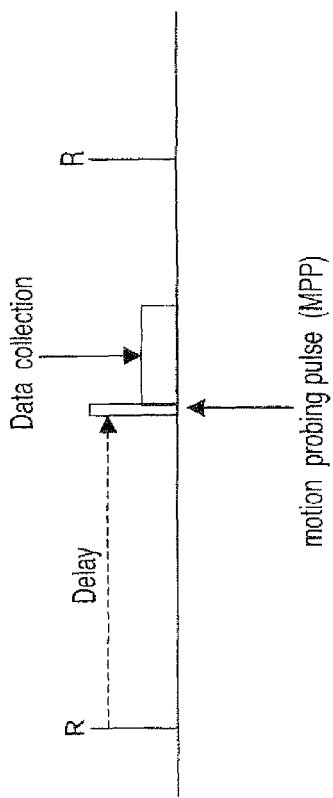
FIG. 12 is a view showing a setting example of slabs in the first embodiment.

In this MRI apparatus 100, at the time of WH MRCA, data collection is carried out based on a multi-slab/multi breath-holding method. That is, for example, as shown in FIG. 12, a region including an entire heart is divided into a plurality of slabs S1 to S4, and data collection is individually performed in each of these slabs S1 to S4. Furthermore, like the conventional technology, this data collection is executed when a level of a monitor signal obtained by subjecting an NMR signal acquired from a periphery of a diaphragm or a liver to one-dimensional Fourier transformation falls within an allowable range between an upper threshold value USL and a lower threshold value LSL.

Figure 13:
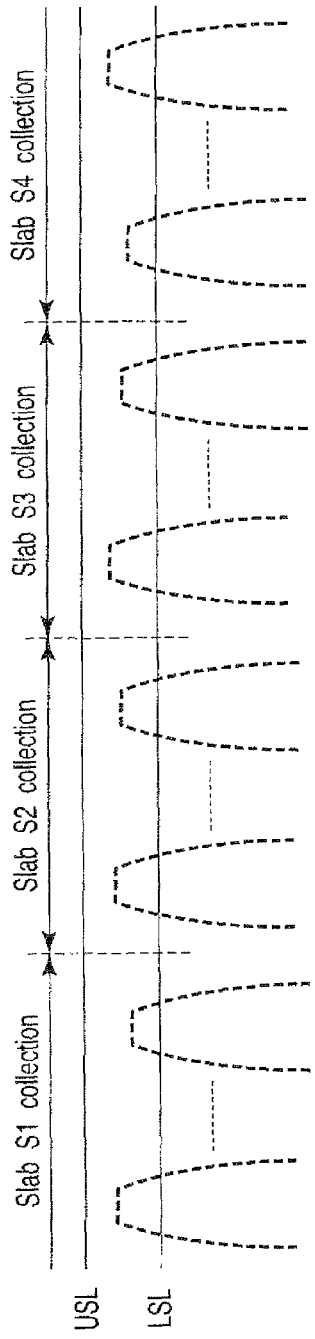
FIG. 13 is a view showing a setting example of an allowable range in the first embodiment.

However, in the first embodiment, as shown in FIG. 13, the main controller 10g applies the upper threshold value USL and the lower threshold value LSL determined based on a respiratory level of the subject 200 before data collection in the first slab S1 to all of the slabs S1 to S4 without change. As to settings of the upper threshold value USL and the lower threshold value LSL, the subject 200 is urged to naturally breathe for several times before scanning in order to statistically obtain, e.g., a mode value of the respiratory level, and the threshold values can be set so that a preset allowable margin (e.g., 5 mm) can be acquired with the mode value as a reference (at the center). The upper threshold value USL and the lower threshold value LSL may be set by an operator or may be automatically set under control of the main controller 10g. At this time, the respiratory level of the subject 200 may be judged by using the NMR signal or a signal of a respiratory synchronizer (e.g., a bellows).

Figure 14:
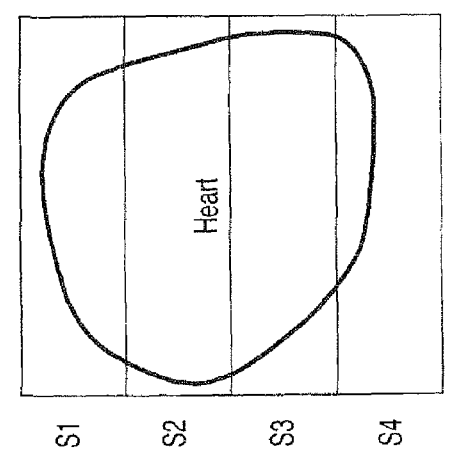
FIG. 14 is a view showing an example of a sequence concerning collection of an NMR signal.

FIG. 14 is a view showing an example of a sequence concerning collection of the NMR signal.

This imaging method is usually carried out with electrocardiographic synchronization. Furthermore, after a fixed delay time passes from an R wave, a motion probing pulse (MPP) is collected as the NMR signal to obtain the monitor signal. This collection of the MPP is carried out without applying a phase encoding gradient magnetic field Ge. Moreover, after collecting the MPP, data collection for imaging is performed. In this data collection for imaging, the phase encoding gradient magnetic field Ge is applied.

On the other hand, during execution of WH MRCA in such a conformation, the main controller 10g generates an image indicating whether the respiratory level of the subject 200 falls within the allowable range. The image is, e.g., such an image as depicted in FIG. 13 showing the monitor signal, the upper threshold value USL, and the lower threshold value LSL. The main controller 10g displays this image in the display unit 10e to allow an operator to confirm. Additionally, the main controller 10g supplies an image signal indicating the image to the electric-optical signal converter 11a through the interface unit 10a. This image signal is converted into an optical signal by the electric-optical signal converter 11a to be transmitted through the optical cable 11b, and led into the shielded room R1. Further, the image signal is again converted into an electric signal by the optical-electric signal converter 11c in the shielded room R1 to be supplied to the display device 12a. Thus, the display device 12a displays the image indicated by this image signal. The image displayed in the display device 12a is reflected by the mirror 12b to be visually recognized by the subject 200.

Therefore, the subject 200 can confirm whether his/her respiratory level at the present time falls within the allowable range by confirming reflection of the image in the mirror 12b. Furthermore, the subject 200 can hold breathing in a state where his/her respiratory level falls within the allowable range.

Thus, in the MRI apparatus 100, data collection can be assuredly performed every time the subject 200 holds breathing, thereby improving an efficiency of data collection. Moreover, since data collected every time breathing is held can be obtained in a respiratory state in the fixed allowable range in each of the plurality of slabs, a 3D image finally obtained based on data collected with respect to each of the plurality of slabs is a high-quality image with less registration error or blurring.

Additionally, in the MRI apparatus 100, the image signal generated outside the shielded room R1 is led into the shielded room R1 as the optical signal. As a result, noise and others from the shielded room R1 can be prevented from affecting collection of the NMR signal.

(Second to Fourth Embodiments)

Figure 30:
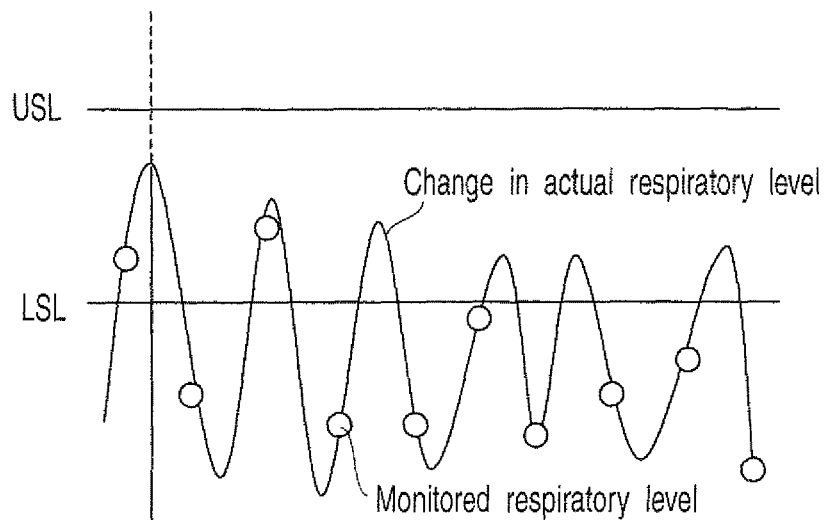
FIG. 30 is a view showing a relationship between a change in an actual respiratory level and a monitored respiratory level.

Meanwhile, in the first embodiment, collection of the NMR signal for acquisition of positional information is performed only once per heart rate. That is, the respiratory level is monitored only once or twice per respiration as shown in FIG. 30, the subject may not recognize a change in respiration even if the subject is informed of the monitored respiratory level alone. That is, an interval of updating information acquired in the above-explained cycle may be too long as an interval of updating information required to control the respiratory level. In other words, a feedback time constant in respiratory level control is long.

Under such circumstances, it can be considered that adjustment of the respiratory level by the subject based on the monitored respiratory level is similar to a case where the feedback time constant in automatic control is long, and under-control or over-control may possibly occur.

Thus, second to fourth embodiments that avoid such an inconvenience will now be explained hereinafter.

Figure 31:
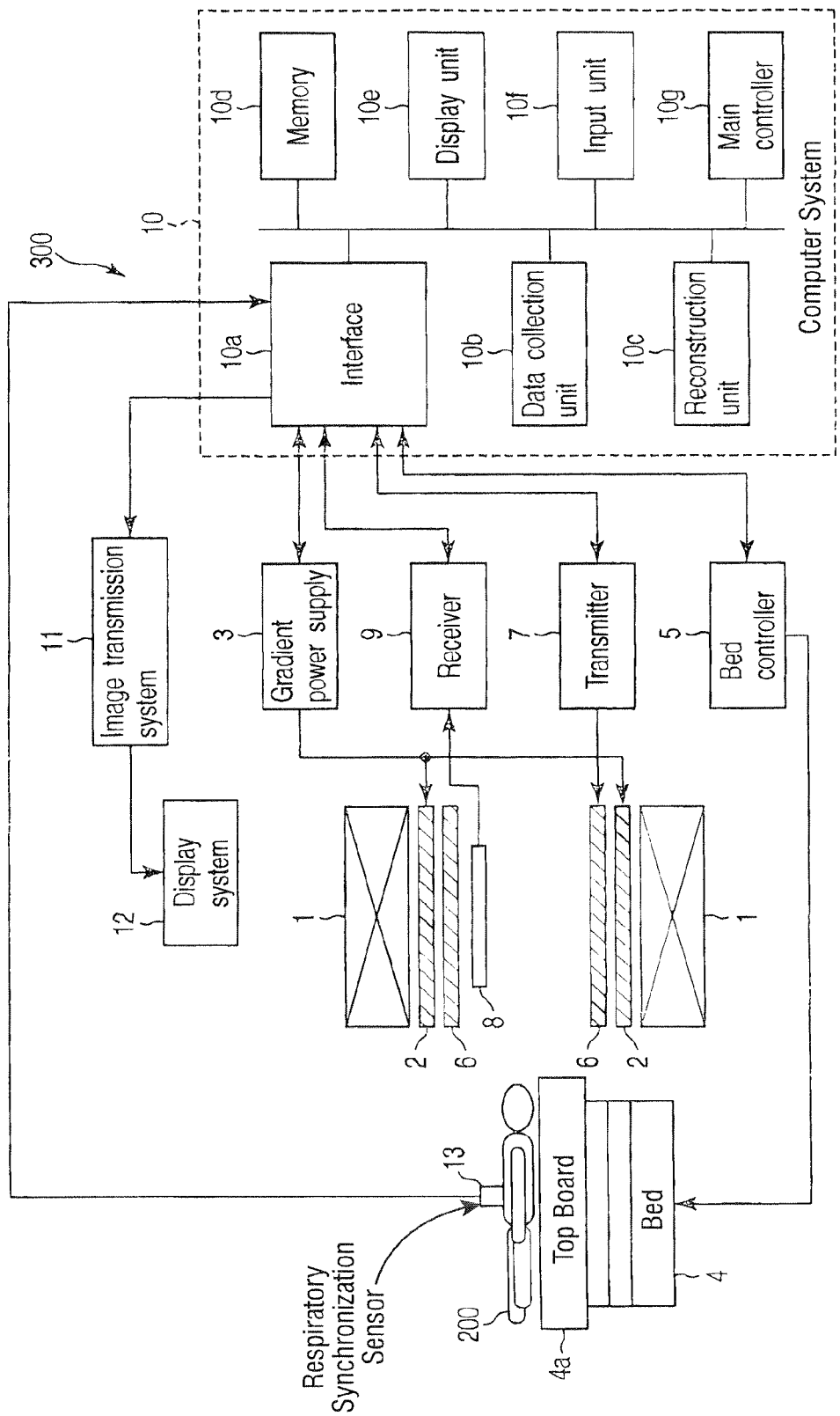
FIG. 31 is a view sowing a structure of a magnetic resonance imaging apparatus according to each of second to fourth embodiments of the present invention.

FIG. 31 is a view showing a structure of a magnetic resonance imaging apparatus (an MRI apparatus) 300 according to each of the second to fourth embodiments. It is to be noted that, in FIG. 31, like reference numbers denote parts equal to those in FIG. 9, thereby omitting a detailed explanation thereof.

The MRI apparatus 300 includes a static field magnet 1, a gradient coil unit 2, a gradient power supply 3, a bed 4, a bed controller 5, a transmitting RF coil 6, a transmitter 7, a receiving RF coil 8, a receiver 9, a computer system 10, an image transmission system 1, a display system 12, and a respiratory synchronization sensor 13.

That is, the MRI apparatus 300 includes the respiratory synchronization sensor 13 in addition to the respective elements included in the MRI apparatus 100.

The respiratory synchronization sensor 13 is disposed to an abdominal of a subject 200 to detect a respiratory level of the subject 200 based on a physical movement of the abdominal of the subject 200.

(Second Embodiment)

A main controller 10g in the second embodiment includes a plurality of functions mentioned below. It is to be noted that the plurality of functions can be realized by allowing a processor included in the main controller 10g to execute a program.

As one of the functions, each relevant section is controlled to enable a data collection unit 10b to obtain an NMR signal required to detect a respiratory level of the subject 200 (which will be referred to as a monitoring NMR signal hereinafter). As one of the functions, the respiratory level of the subject 200 is detected based on the monitoring NMR signal acquired by the data collection unit 10b. As one of the functions, each relevant section is controlled to enable the data collection unit 10b to collect an NMR signal required to reconstruct an image (which will be referred to as a reconstruction NMR signal hereinafter) when the respiratory level detected based on the monitoring NMR signal falls within an allowable range. As one of the functions, a display image obtained by combining a respiratory waveform representing a change in the respiratory level detected by the respiratory synchronization sensor 13 with an image indicating the respiratory level detected based on the monitoring NMR signal is generated. It is to be noted that the respiratory level detected based on the monitoring NMR signal will be referred to as a first respiratory level and the respiratory level detected by the respiratory synchronization sensor 13 will be referred to as a second respiratory level hereinafter.

In this MRI apparatus 300 according to the second embodiment, WH MRCA is executed based on a known sequence. During such WH MRCA, the main controller 10g generates a display image that informs the subject 200 of whether the respiratory level of the subject 200 falls within the allowable range as follows. It is to be noted that, in WH MRCA, the monitoring NMR signal is acquired. The monitoring NMR signal is an NMR signal collected from an excitation slice or an excitation slab including a target part such as a diaphragm. The monitoring NMR signal can be acquired without applying, e.g., a phase encoding gradient magnetic field. As the monitoring NMR signal, an MPP can be used like the first embodiment, for example.

The main controller 10g acquires the second respiratory level detected by the respiratory synchronization sensor 13 at a rate that is sufficient to reproduce a respiratory waveform. It is to be noted that the respiratory synchronization sensor 13 can continuously detect the respiratory level in an actual time by using, e.g., a bellows.

Figure 32:
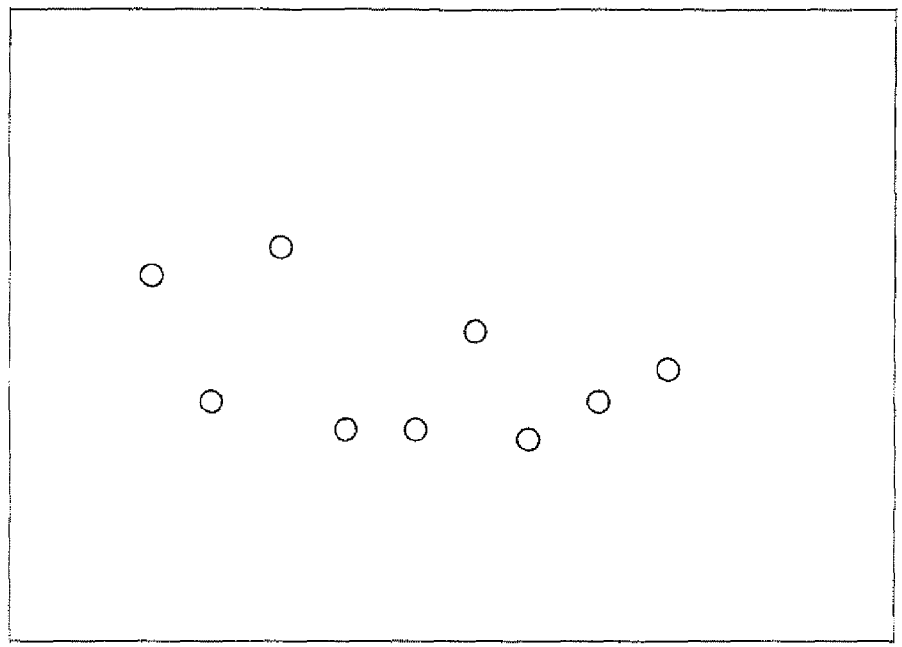
FIG. 32 is a view showing an example of a first image in the second embodiment.

The main controller 10g detects the first respiratory level once per heart rate in control for WH MRCA. The main controller 10g generates such a first image as shown in FIG. 32 in which each first respiratory level acquired in a recent fixed period is arranged on a plane defined by a time axis and a respiratory level axis.

Figure 33:
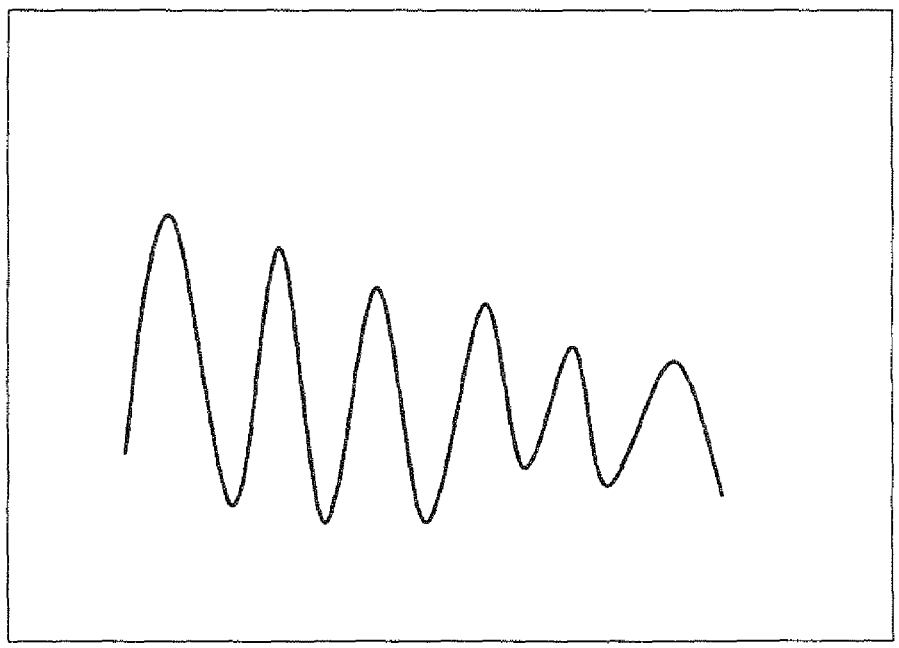
FIG. 33 is a view showing an example of a second image in the second embodiment.

On the other hand, the main controller 10g generates such a second image as shown in FIG. 33 representing a respiratory waveform in the period based on the second respiratory level acquired in the fixed period.

Further, the main controller 10g generates a display image as an image obtained by combining the first image with the second image. At this time, the main controller 10g normalizes respective amplitude scales (a maximum value and a minimum value of each amplitude) of the first respiratory level and the second respiratory level to be combined with each other.

The main controller 10g updates the display image every time the second respiratory level is acquired. Thus, the display image is an image in which the respiratory waveform scrolls with elapse of time.

Figure 34:
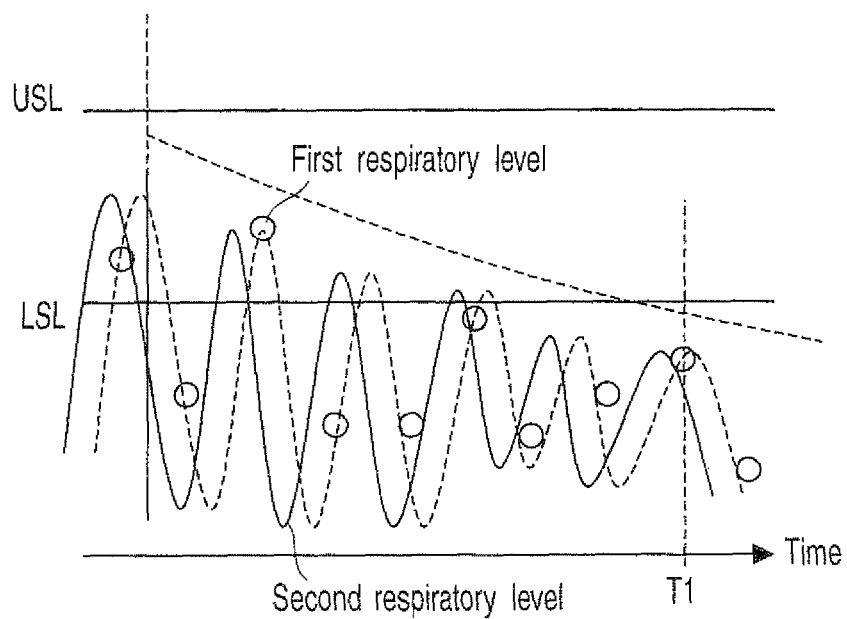
FIG. 34 is a view showing a delay of a first respiratory level with respect to a second respiratory level in the second embodiment.

Meanwhile, since the monitoring NMR signal is acquired and the first respiratory level is obtained based on this monitoring NMR signal, detection of the first respiratory level requires a slight amount of time. Therefore, detection of the first respiratory level has actual time properties lower than those of detection of the second respiratory level. Therefore, as shown in FIG. 34, the first respiratory level has a fixed delay with respect to the second respiratory level. Thus, the main controller 10g combines the first image with the second image to correct this delay.

That is, it is assumed that a display image immediately before the first respiratory level is newly detected is as shown in FIG. 35. Furthermore, when updating the display image after the first respiratory level is newly detected, the display image is updated in such a manner that the newly detected respiratory level is not displayed as information at the present time but it is displayed as information at a time point reached by traveling back in time by an amount corresponding to the delay as shown in FIG. 36.

The thus generated display image is transmitted to the display system 12 through the interface unit 10a and the image transmission system 11, and this display system 12 displays this display image so that the subject 200 can visually recognize.

As explained above, according to the second embodiment, in the display image, the first respiratory level detected based on the monitoring NMR signal and the second respiratory level detected based on the respiratory synchronization sensor 13 are simultaneously shown. Therefore, the subject 200 can recognize a state of a change in the respiratory level based on the respiratory waveform in this display image and an accurate respiratory level based on display of the second respiratory level. As a result, the subject 200 can accurately grasp an actual state of respiration, thereby appropriately adjusting respiration.

(Third Embodiment)

In the third embodiment, a main controller 10g includes a plurality of functions mentioned below. It is to be noted that the plurality of functions can be realized by allowing a processor included in the main controller 10g to execute a program.

As one of the functions, relevant respective sections are controlled so that a data collection unit 10b can acquire a monitoring NMR signal. As one of the functions, a first respiratory level is detected based on the monitoring NMR signal. As one of the functions, relevant respective sections are controlled so that the data collection unit 10b can collect a reconstruction NMR signal when the respiratory level detected based on the monitoring NMR signal falls within an allowable range. As one of the functions, relevant respective sections are controlled so that the data collection unit 10b can acquire an NMR signal that is used to detect a respiratory level for display (which will be referred to as a display NMR signal hereinafter). As one of the functions, a respiratory level of a subject 200 (which will be referred to as a second respiratory level hereinafter) is detected based on the display NMR signal. As one of the functions, a display image indicating the first respiratory level and the second respiratory level is generated.

Figure 37:
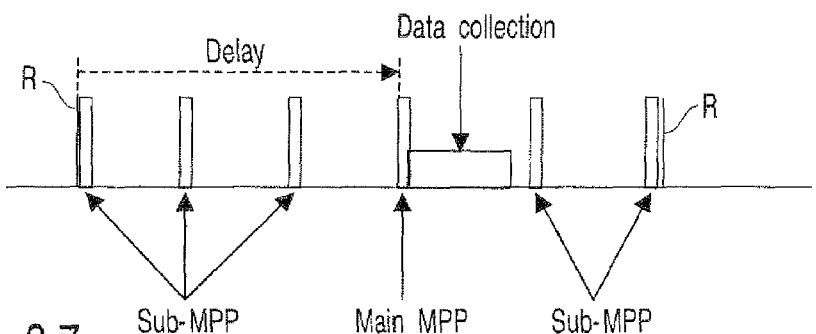
FIG. 37 is a view showing a sequence when WH MRCA is performed in the third embodiment.

In the MRI apparatus 300 according to the third embodiment, when executing WH MRCA, the main controller 10g allows the data collection unit 10b to collect the NMR signal based on such a sequence as depicted in FIG. 37.

In the sequence shown in FIG. 37, a plurality of MPPs is collected in one heart rate. The plurality of MPPs is classified into a main MPP and a sub-MPP. The main PP is collected immediately before a data collection period in an imaging region. The sub-MPP is collected at a timing different from that of the main MPP while avoiding the data collection period. The sub-MPP may be collected either before or after the main MPP in any period excluding the data collection period in the imaging region. For example, the plurality of sub-MPPs may be collected before the main MPP. Further, the plurality of MPPs may be collected at equal intervals within one heart rate (including not only the sub-MPP but also the main MPP). In this case, when any one of the plurality of MPPs set at equal intervals is included in the data collection period in the imaging region, this MPP is not collected.

The main MPP corresponds to the MPP acquired in the sequence depicted in FIG. 14, and it is used as the monitoring NMR signal. The sub-MPP is added and acquired irrespective of the purpose of control of WH MRCA, and it is used as the display NMR signal.

Figure 38:
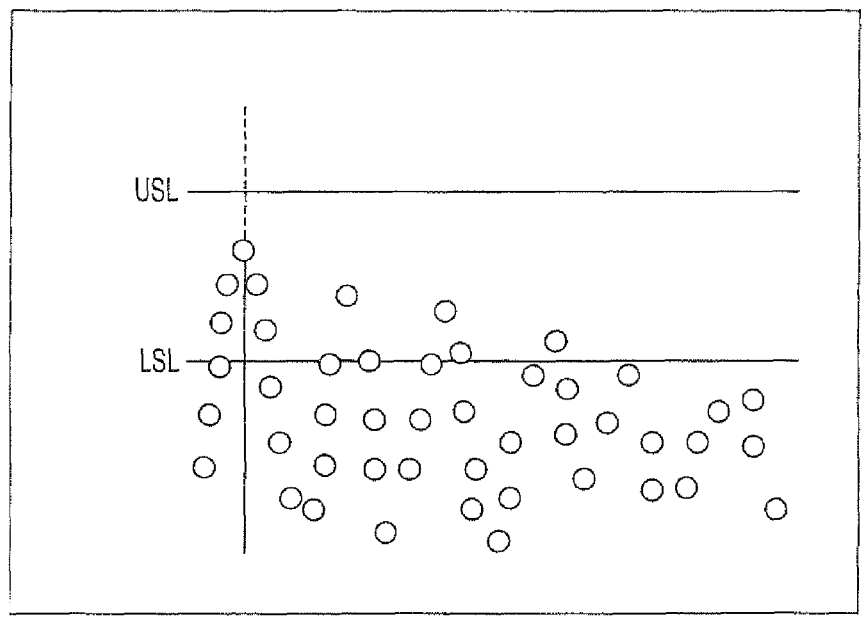
FIG. 38 is a view showing an example of a display image in the third embodiment.

Furthermore, the main controller 10g detects the first respiratory level for WH MRCA based on the monitoring NMR signal alone. The main controller 10g detects the second respiratory level likewise based on the display NMR signal, though this signal is not used for WH MRCA. Moreover, the main controller 10g generates, e.g., such a display image as depicted in FIG. 38 in which the first respiratory level and the second respiratory level acquired in a recent fixed period are respectively arranged on a plane defined by a time axis and a respiratory level axis.

The thus generated display image is transmitted to a display system 12 through an interface unit 10a and an image transmission system 11, and this display system 12 displays this display image in a state where the subject 200 can visually recognize it.

As explained above, according to the third embodiment, in the display image, many respiratory levels respectively detected in a short period are shown in time-series. Therefore, the subject 200 can recognize a state of a change in the respiratory level from this display image. As a result, the subject 200 can accurately grasp an actual state of respiration, thereby appropriately adjusting respiration.

(Fourth Embodiment)

In the fourth embodiment, a main controller 10g includes a plurality of functions mentioned below. It is to be noted that the plurality of functions can be realized by allowing a processor included in the main controller 10g to execute a program.

As one of the functions, relevant respective sections are controlled so that a data collection unit 10b can collect a monitoring NMR signal. As one of the functions, a respiratory level of a subject 200 is detected based on the monitoring NMR signal. As one of the functions, relevant respective sections are controlled so that the data collection unit 10b can collect a reconstruction NMR signal when the respiratory level detected based on the monitoring NMR signal falls within an allowable range. As one of the functions, a display image showing the latest detected respiratory level and a maximum value of detection levels detected within a predetermined period is generated.

In the MRI apparatus 300 according to the fourth embodiment, WH MRCA is executed in accordance with a known sequence. During execution of such WH MRCA, the main controller 10g generates a display image that informs the subject 200 of whether the respiratory level of the subject 200 falls within the allowable range as follows.

The main controller 10g detects the respiratory level once per heart rate in control for WH MRCA. The main controller 10g generates a display image indicating a detected respiratory level every time the respiratory level is newly detected.

Figure 39:
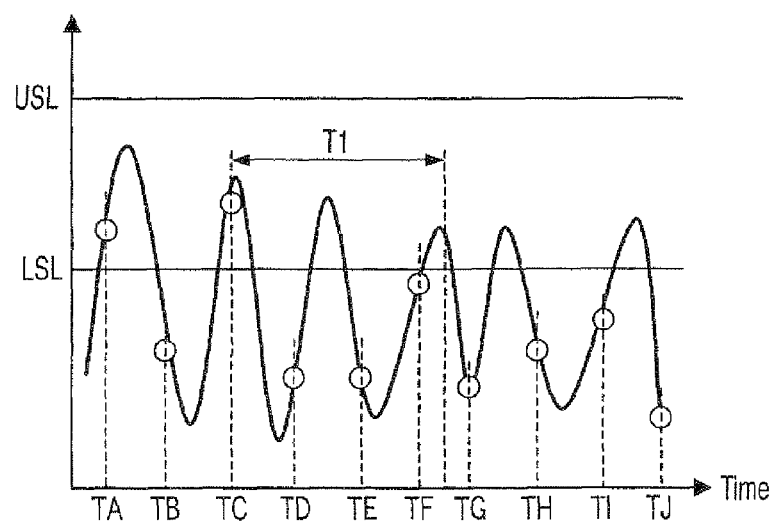
FIG. 39 is a view showing an example of a respiratory level detection state in the fourth embodiment.

For example, as shown in FIG. 39, the main controller 10g generates such a display image IA as depicted in FIG. 40 in accordance with detection of such a respiratory level as depicted in FIG. 39 at a time point TA. In the display image IA, the respiratory level detected at the time point TA is indicated by a black dot.

On the other hand, in accordance with detection of such a respiratory level as depicted in FIG. 39 at a time point TB, the main controller 10g generates a display image IB in which the respiratory level detected at the time point TB is indicated by the black dot as shown in FIG. 40. Meanwhile, the detection level detected at the time point TB is lower than the detection level detected at the time point TA. In such a case, the main controller 10g indicates the detection level detected at the time point TA as a recent maximum level in the display image IB. It is to be noted that the maximum level is indicated as a dot with hatching in FIG. 40.

In accordance with detection of such a respiratory level as shown in FIG. 39 at time point TC, the main controller 10g generates a display image IC in which the respiratory level detected at a time point TC is indicated by the black dot as shown in FIG. 40. Since the respiratory level detected at the time point TC is higher than the maximum level obtained thus far, the maximum level is not shown in the display image IC.

Thereafter, display images ID to IF in FIG. 40 are likewise generated at time points TD to TF in FIG. 39, respectively.

In accordance with detection of such a respiratory level as shown in FIG. 39 at a time point TG, the main controller 10g generates a display image IG in which the respiratory level detected at the time point TG is indicated by the black dot as depicted in FIG. 40. Meanwhile, the maximum level obtained thus far is the respiratory level detected at the time point TC but, at the time point TG, a specified time T1 or more elapses from the time point TC. In such a case, the main controller 10g cancels the last maximum level, and does not show this level in a newly generated image.

Thereafter, display images IH to IJ in FIG. 40 are likewise generated at time points TH to TJ in FIG. 39, respectively.

The thus generated display images are transmitted to a display system 12 through an interface unit 10a and an image transmission system 11, and this display system 12 sequentially displays these display images in a state where the subject 200 can visually recognize them.

As explained above, according to the fourth embodiment, the latest detected respiratory level and a maximum respiratory level detected in a recent fixed period are shown in the display image. Therefore, the subject 200 can recognize from this display image a relationship between the current respiratory level and the recent maximum level. As a result, the subject 200 can accurately grasp an actual state of respiratory, thereby appropriately adjusting respiration.

Each of the foregoing embodiments can be modified in many ways as follows.

(1) In each embodiment, the image signal may be generated by using, e.g., a CCD (charge-coupled device) camera to image a picture displayed in the display unit 10e.

(2) In each embodiment, as indicated by a broken line in FIG. 10, the display device 12a may be arranged on the bed-side opening 20b side in a posture that the display plane thereof becomes substantially orthogonal to the central axis of the imaging space 20a and faces the imaging space 20a. Alternatively, the display device 12a may be arranged on the bed-side opening 20b side in a posture that the display plane thereof becomes substantially parallel to the central axis of the imaging space 20a. When the display device 12a is arranged in the posture that the display plane thereof becomes substantially parallel to the central axis of the imaging space 20a, the mirror 12c reflects an image displayed in the display device 12a toward the mirror 12b. However, when the display device 12a is arranged on the bed-side opening 20b side, a direction of the mirror 12b is changed as indicated by a broken line in FIG. 11. The direction of the mirror 12b may be fixed or may be variable.

Figure 15:
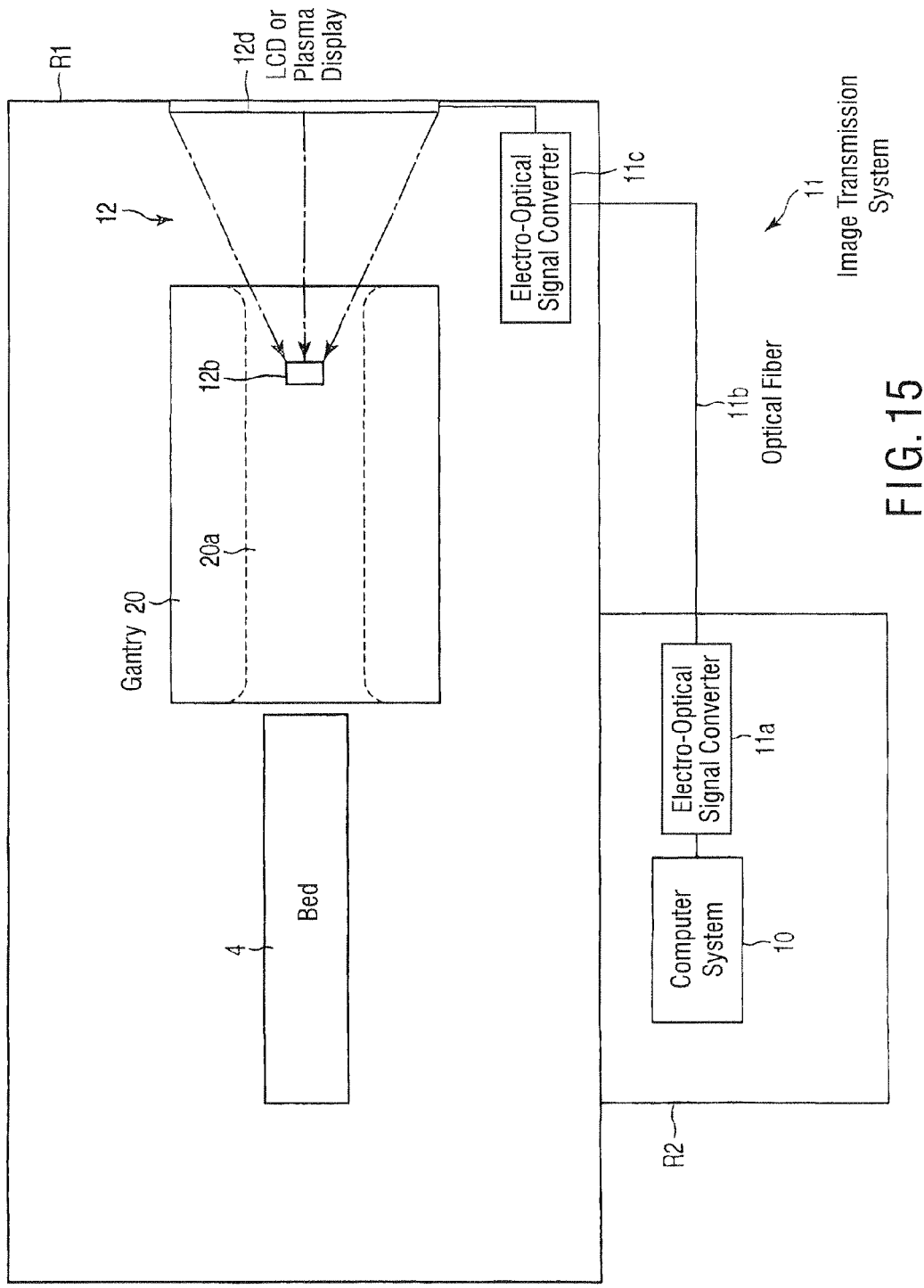
FIG. 15 is a view showing a modified structural example of the display system in FIG. 9.

(3) In each embodiment, a large-screen display (e.g., a liquid crystal or a plasma) 12d may be used in place of the display device 12a as shown in FIG. 15.

Figure 16:
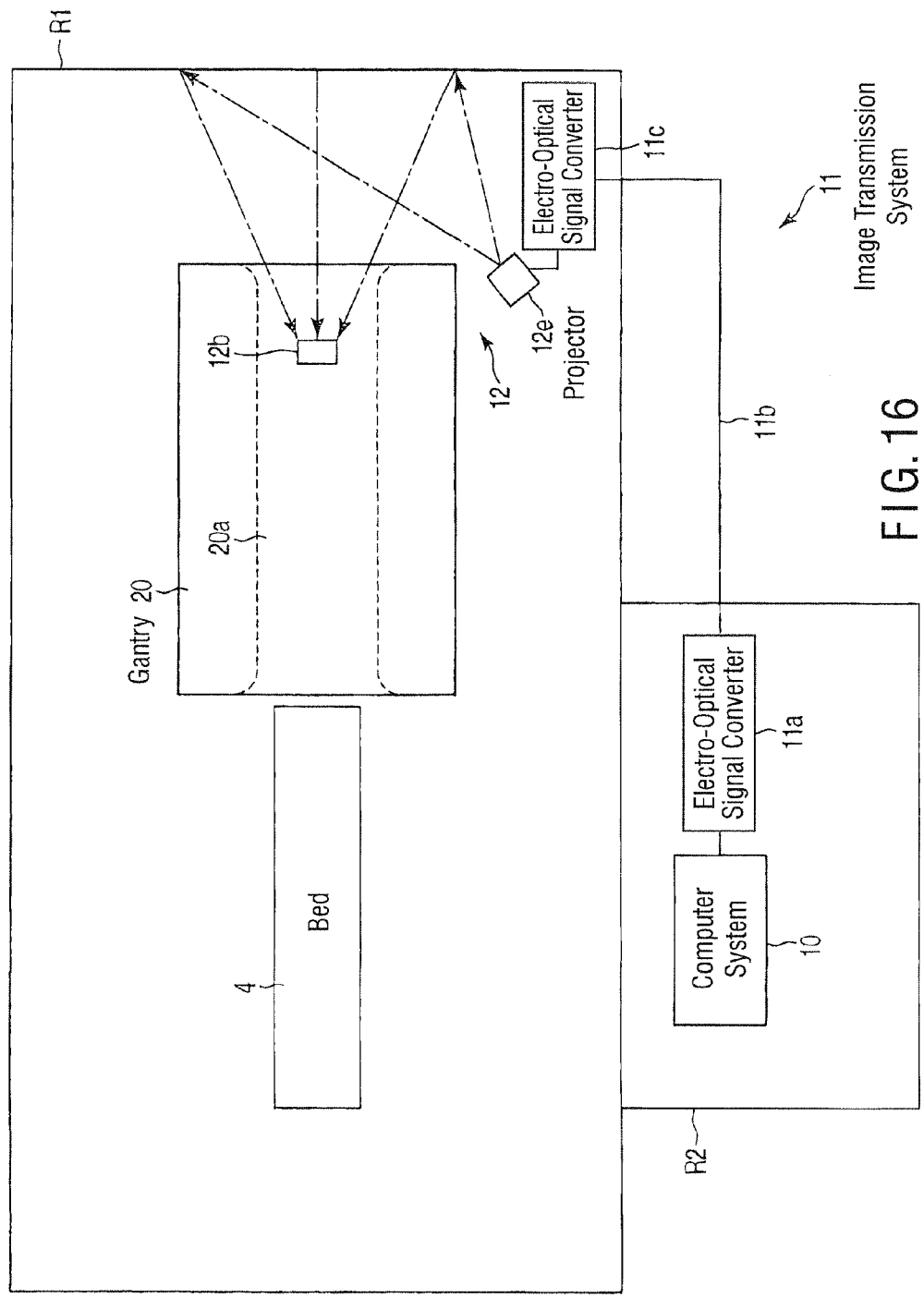
FIG. 16 is a view showing a modified structural example of the display system in FIG. 9.

(4) In each embodiment, a projector 12e may be used in place of the display device 12a as shown in FIG. 16 to project an image indicated by the image signal onto a wall of the shielded room R1. When using the projector 12e, an image may be directly projected onto the mirror 12b, or the mirror 12b may be omitted to project an image onto a wall surface of the gantry 20 around the imaging space 20a. A plotting device obtained by combining a laser emitting device and a movable mirror may be used in place of the display device 12a and the mirror 12b to plot an image on the wall surface of the gantry 20.

(5) In each embodiment, the display device 12a may be arranged in the imaging space 20a. In this case, the mirror 12b may be omitted to allow the subject 200 to directly visually observe an image displayed in the display device 12a. Further, in this case, disposing a liquid crystal sheet or an organic electroluminescent (EL) panel on the wall surface of the gantry 20 around the imaging space 20a can be considered.

(6) In each embodiment, an image generated outside the shielded room R1 may be led into the shielded room R1 to be visually observed by the subject 200.

Figure 17:
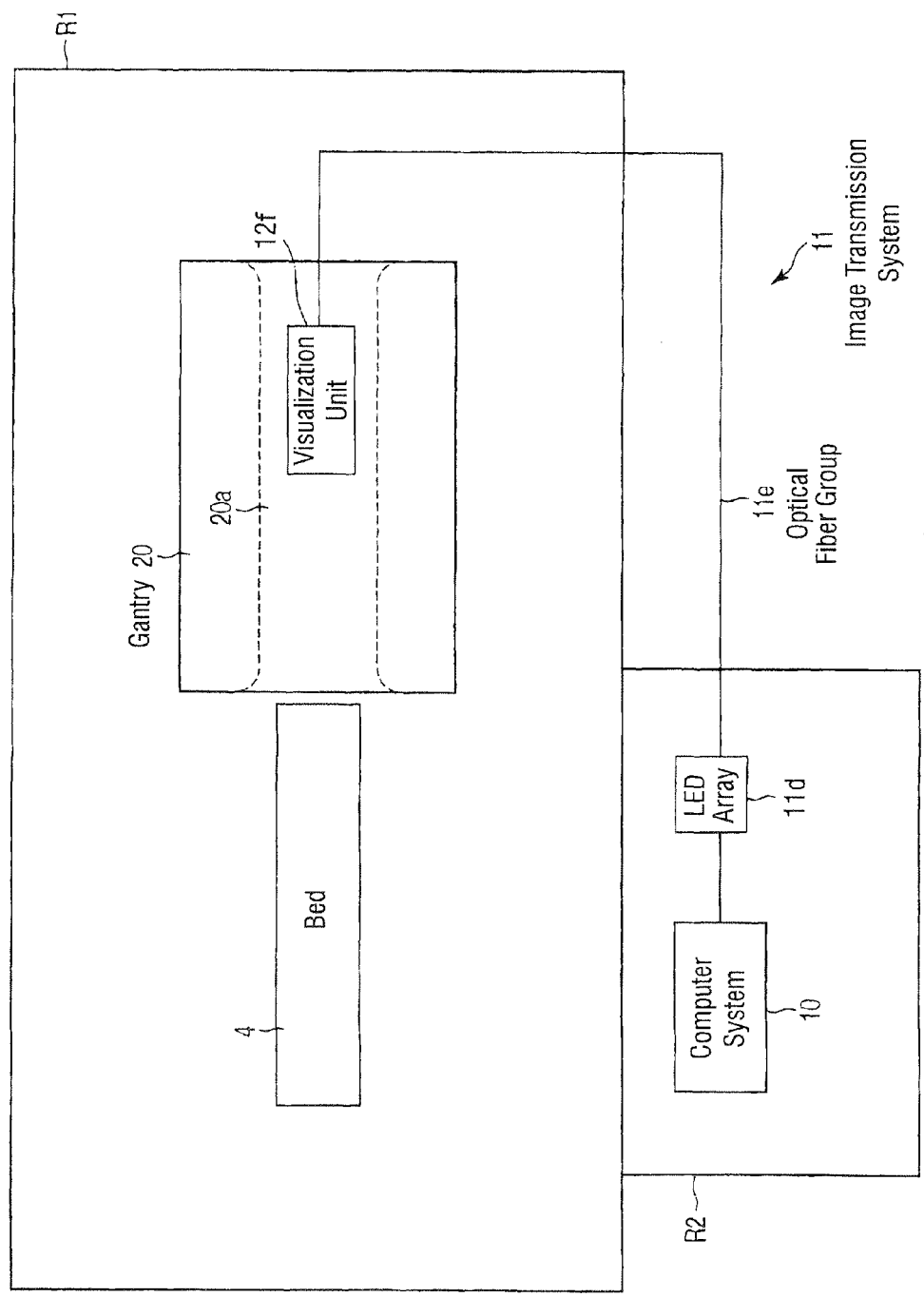
FIG. 17 is a view showing modified structural examples of the image transmission system and the display system in FIG. 9.

For example, as shown in FIG. 17, the image transmission system 11 is configured to include a light-emitting diode (LED) array 11d and an optical cable group (an optical fiber group) 11e, and the display system 12 is configured to include a visualization unit 12f.

The LED array 11d has many LEDs one-dimensionally or two-dimensionally arranged therein, and reproduces an image indicated by the image signal. The optical cable group 11e is obtained by bundling many optical cables, and transmits the image reproduced by the LED array 11d as it is. The visualization unit 12f allows the subject to visually observe the image transmitted through the optical cable group 11e.

Figures 18, 20:
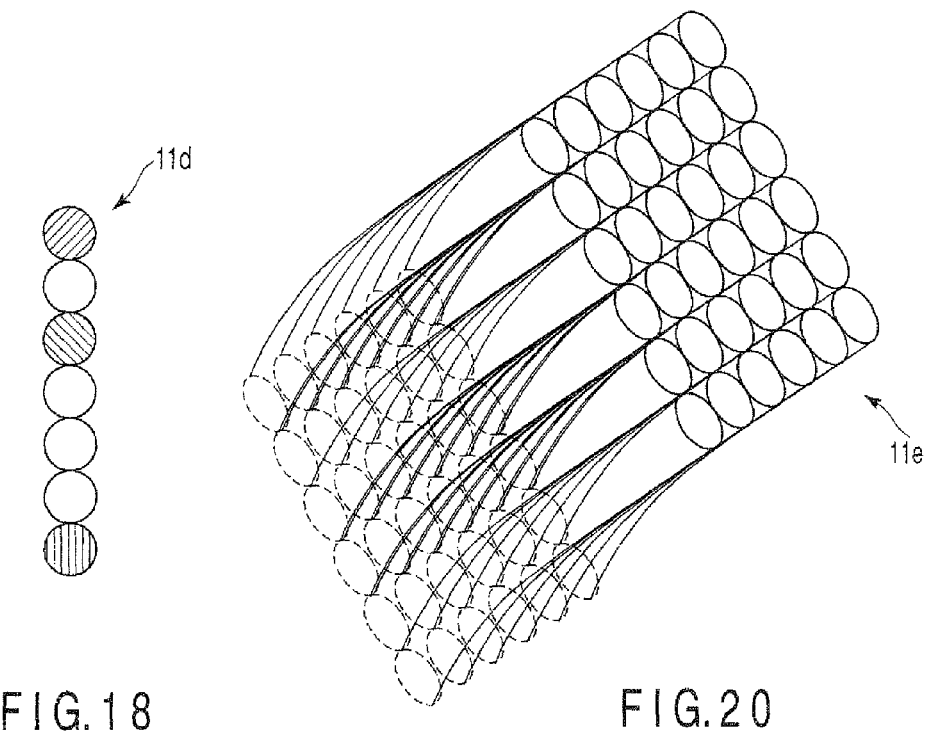
FIG. 18 is a view showing an example of an image reproduction state in an LED array in FIG. 10 obtained by one-dimensionally aligning LEDs.
FIG. 20 is a view showing an example of a structure of an optical cable group having an end portion functioning as a visualization unit section in FIG. 17.

FIG. 18 is a view showing an example of a reproduction state of an image in the LED array lid having the LEDs one-dimensionally arranged therein. It is to be noted that one circle in FIG. 18 represents one LED. In FIG. 18, turning on the LEDs at both ends in a blue color or a yellow color represents the upper threshold value USL and the lower threshold value LSL, and turning one of the five inner LEDs in a red color represents a current level of a current monitor signal. When the current level of the monitor signal is out of the allowable range, none of the five inner LEDs is turned on.

Figures 19, 21:
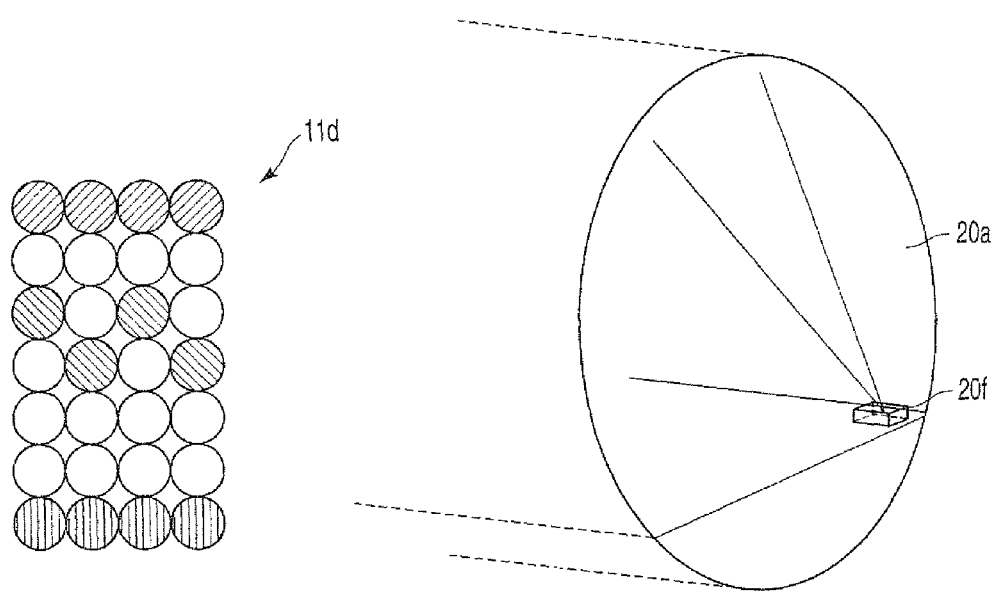
FIG. 19 is a view showing an example of an image reproduction state in the LED array in FIG. 10 obtained by two-dimensionally aligning the LEDs.
FIG. 21 is a view showing a specific structural example of the visualization unit in FIG. 17.

FIG. 19 is a view showing an example of a reproduction state of an image in the LED array lid having the LEDs two-dimensionally arranged therein. It is to be noted that one circle in FIG. 19 represents one LED. In FIG. 19, four LED strings each having an alignment depicted in FIG. 18 are arranged. A change in level of the monitor signal is represented by using each of the four LED strings like the above example.

When facets of many optical cables included in the optical cable group 11e are one-dimensionally or two-dimensionally arranged, the visualization unit 12f can be configured to visualize an image by using an alignment of lights emitted from these optical cables.

FIG. 20 is a view showing an example of a structure of the optical cable group 11e having an end portion functioning as the visualization unit 12f.

Alternatively, the visualization unit 12f may be arranged in the imaging space 20a as shown in FIG. 21 to project an image onto the wall surface of the gantry 20 on the upper side of the imaging space 20a.

Figure 22:
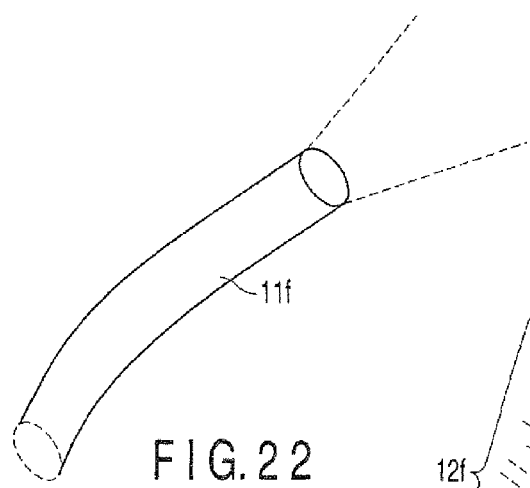
FIG. 22 is a view showing a fiber scope that can be used in place of the optical cable group in FIG. 17.

Alternatively, such a fiber scope 11f as shown in FIG. 22 may be used in place of the optical cable group 11e to guide an image reproduced by the LED array 11d to eyes of the subject 200.

Figure 24:
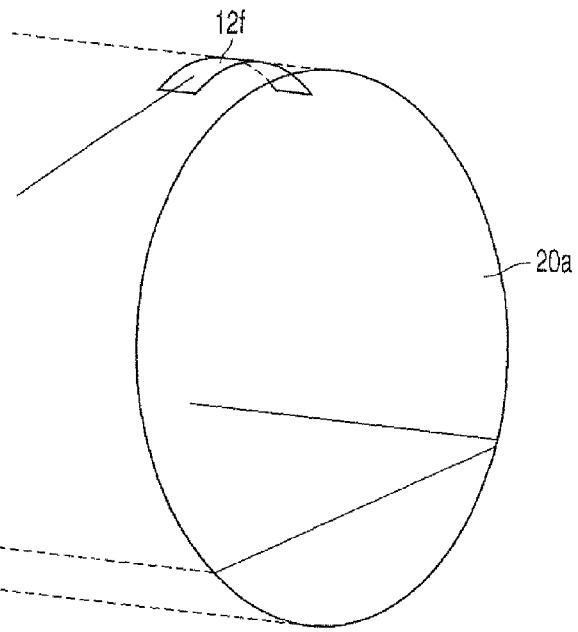
FIG. 24 is a view showing an arrangement example of the visualization unit depicted in FIG. 23.
Figure 23:
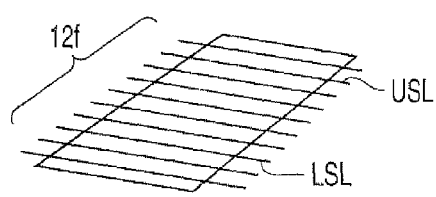
FIG. 23 is a view showing a specific structural example of the visualization unit in FIG. 17.

Such a semitransparent optical cable array as shown in FIG. 23 may be used as the visualization unit 12f, and it may be disposed on the wall surface of the gantry 20 on the upper side of the imaging space 20a as depicted in FIG. 24.

Figure 25:
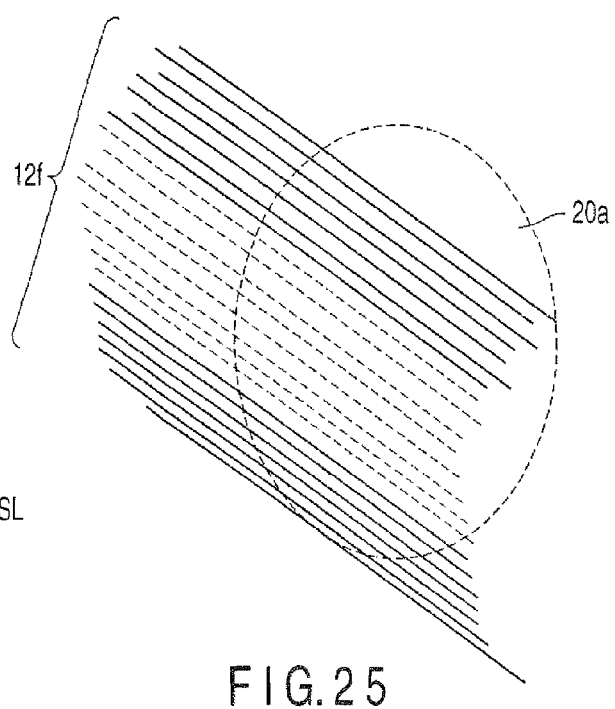
FIG. 25 is a view showing an arrangement example when a semitransparent optical cable array is used as the visualization unit in FIG. 17.

The semitransparent optical cable array as the visualization unit 12f may be arranged to match an arrangement direction of the semitransparent optical cable to a circumferential direction of the wall surface of the gantry around the imaging space 20a as depicted in FIG. 25.

Figure 26:
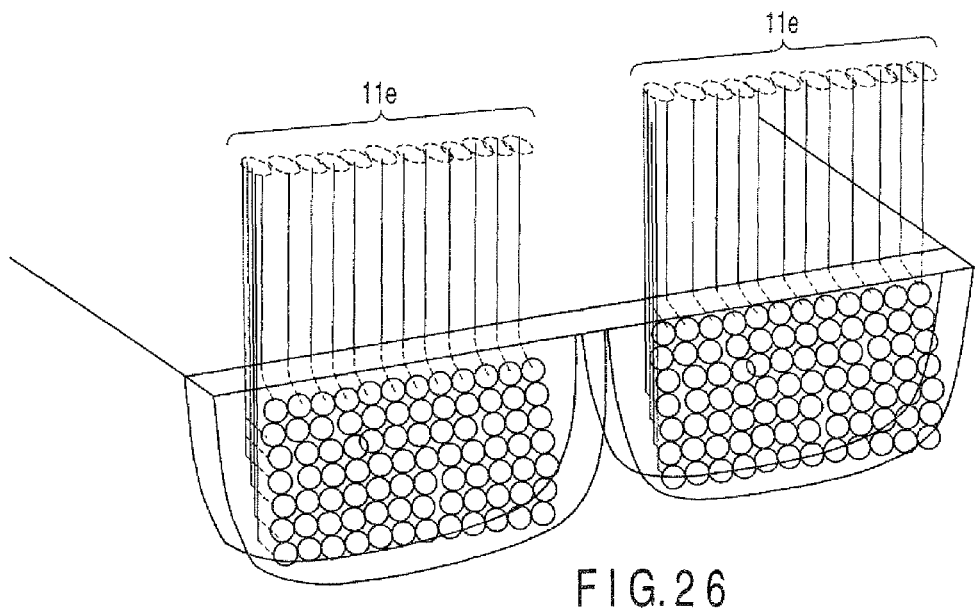
FIG. 26 is a view showing a modified structural example of the visualization unit.

The visualization unit 12f may be configured like glasses in which end portions of the optical cable groups 11e are arranged in lens portions as shown in FIG. 26, and this unit may be put on a face of the subject 200.

(7) In each embodiment, the image transmission technology explained in (6) may be used to lead an image displayed in the display unit 10e or an image displayed in the display device 12a to the imaging space 20a, thereby allowing the subject 200 to visually observe the image.

In this case, as shown in FIG. 27, an input end of the optical cable group 11e is appressed against the display unit 10e or the display device 12a to enable incidence of an upper part of the image displayed in the display unit 10e or the display device 12a without loss. At this time, using a lens or an auxiliary optical guide medium is also useful. Furthermore, a glass with a lens or a diffusion glass is preferable as the visualization unit 12f.

Moreover, when using the fiber scope 11f in place of the optical cable group 11e, as shown in FIG. 28, an image displayed in the display unit 10e or the display device 12a is reduced in size by a reducing lens 11g to enter the fiber scope 11f, and the image exiting the fiber scope 11f is expanded by a magnifying lens 11h to enter the visualization unit 12f.

Figure 29:
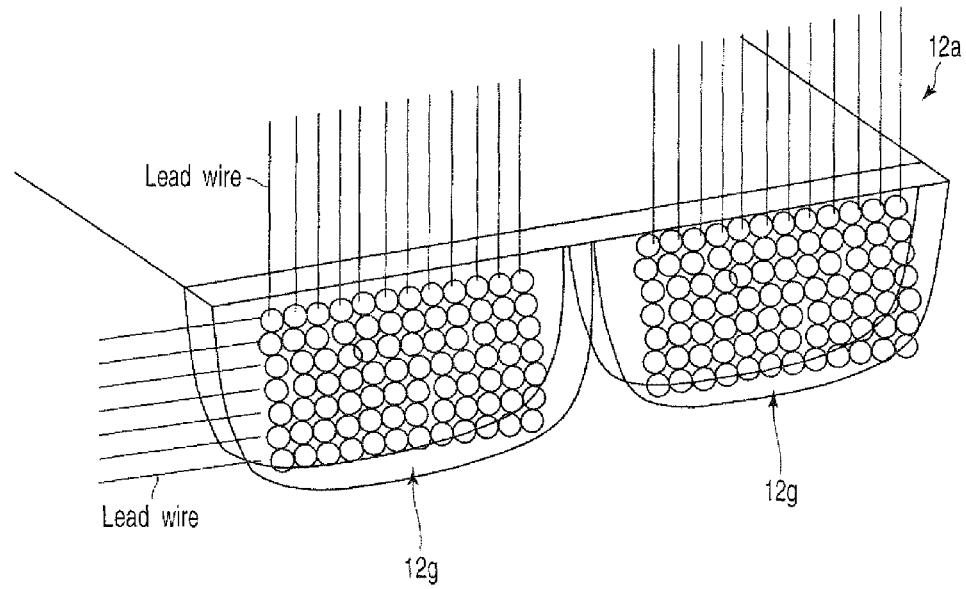
FIG. 29 is a view showing a modified structural example of a display device in FIG. 10.

(8) In each embodiment, the display device 12a may be configured like glasses having the LED arrays 12g contained in lens portions as shown in FIG. 29, and this unit may be put on the face of the subject 200.

(9) In the first embodiment, several respiratory patterns may be registered as ideal states in advance, and one of these patterns may be used as a guide pattern to display an image that can show this pattern and a measured actual respiratory pattern in comparison with each other. As a result, the subject 200 can be guided to approximate a respiratory pattern of the subject 20 to the ideal pattern. That is, a so-called external guiding method can be appropriately executed. It is to be noted that the guide pattern and the measured pattern may be displayed in different colors. Additionally, an HR (a heart rate) when the subject 200 is at rest may be measured in advance, and a respiratory pattern that enables stably and rapidly is terminating data collection may be selected as a guide pattern by using this HR as a reference.

(10) In each embodiment, display of an image indicating whether the respiratory level falls within the allowable range is effective when applied to a situation using a method other than the multi-slab/multi breath-holding method, i.e., a voluntary breathing method or a single slab/multi breath-holding method as long as it is a method of performing data collection when the respiratory level falls within the allowable range.

(11) In each embodiment, a movement correction method of tracing an imaging region of a heart while tracing a movement of a diaphragm may be also used. When this method is used, since a fluctuation in the respiratory level in the allowable range can be corrected by the movement correction method to highly accurately match positions of multi-slabs, a registration error or blurring in a 3D image can be further reduced.

(12) In the first embodiment, the image transmission system 11 and the display system 12 can be used to inform the subject 200 of various kinds of information in addition information indicating whether the respiratory level falls within the allowable range.

(13) In each embodiment, the image transmission system 11 may lead the image signal that is kept as the electrical signal into the shielded room R1.

(14) In the second embodiment, normalization or delay correction does not have to be performed.

(15) In the third embodiment, the number of times of acquisition of the sub-MPP per heart rate may be an arbitrary number of times that is equal to or above 1.

(16) In the third embodiment, when acquisition of the sub-MPP is performed more than once per heart rate, the respiratory level judged based on the main MPP does not have to be included in the display image.

(17) In the fourth embodiment, when the maximum level and the respiratory level at the present time are displayed in different conformations so that they can be respectively displayed even though both the levels coincide with each other, the subject 200 can further easily understand that the maximum level and the respiratory level at the present time coincide with each other. This can be realized by a change, e.g., showing the maximum level in the form of a horizontal line.

(18) In each embodiment, specific contents of the display image can be arbitrarily changed.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A magnetic resonance imaging apparatus comprising:
   an MRI gantry having a static magnetic field generator, gradient magnetic field generators and at least one radio-frequency (RF) antenna configured to send RF signals into an image volume and to receive RF signals from said image volume and a control system including at least one computer configured to control the MRI gantry components;
   said control system being configured to apply to a subject (a) a uniform static magnetic field, (b) a radio-frequency magnetic field and (c) a gradient magnetic field to the subject in accordance with a predetermined pulse sequence to collect (i) magnetic resonance signals from the subject within one heart beat interval to reconstruct images of each of a plurality of slabs using phase encoding magnetic gradient fields,
   said control system also being configured to collect from said subject during said heart beat period (ii) a magnetic resonance signal to monitor subject motion in response to a first motion probing pulse (MPP) subsequence and (iii) at least one magnetic resonance signal to generate a display to the subject without applying a phase-encoding gradient magnetic field in response to at least one second MPP subsequence;
   said control system being further configured to reconstruct an image of an imaging region containing the plurality of slabs using the collected magnetic resonance signals (i) for reconstruction;
   said control system also being configured to detect a first respiratory level for the subject using the magnetic resonance signal (ii) for monitoring and to detect a second respiratory level for the subject using the at least one magnetic resonance signal (iii) for display;
   said control system being configured to control the reconstruction of an image of the subject using the magnetic resonance signals (i) for reconstruction collected when the detected first respiratory level falls within an allowable range that is set with respect to each of the plurality of slabs; and
   said control system being configured to set a single allowable range that is applied to each of the plurality of slabs using respiratory levels detected before the collection of magnetic resonance signals for a first slab in the plurality of slabs to be imaged begins.

2. The magnetic resonance imaging apparatus according to claim 1, wherein said control system is further configured to inform the subject whether the detected respiratory level falls within the allowable range using the second respiratory level determined by said collected at least one magnetic resonance signal (iii) for display.

3. The magnetic resonance imaging apparatus according to claim 1, wherein said control system is configured to correct the magnetic resonance signals (i) for reconstruction to reduce an influence of a fluctuation in the respiratory level.

4. The magnetic resonance imaging apparatus according to claim 2, wherein the control system comprises:
   display-related components which are disposed in a second room different from a magnetically shielded first room where magnetic signal collection components are disposed and which display-related components are configured to generate an image indicating whether the detected second respiratory level falls within the allowable range;
   transmission components configured to optically transmit the image from the second room to the first room; and
   a display which is disposed in the first room and configured to display the image transmitted through the transmission components to the subject.

5. The magnetic resonance imaging apparatus according to claim 4, wherein:
   the display-related components are configured to generate image information,
   the transmission components are configured to transmit the image information by using an optical signal, and
   the display is configured to reproduce and display the image based on the image information.

6. The magnetic resonance imaging apparatus according to claim 4, wherein:
   the display-related components are configured to generate the image as a visible light image,
   the transmission components are configured to transmit the visible light image, and
   the display is configured to project the visible light image to eyes of the subject.

7. A method for controlling a magnetic resonance imaging (MRI) apparatus configured to apply a uniform static magnetic field to a subject and to apply to the subject a radio-frequency magnetic field and a gradient magnetic field in accordance with a predetermined sequence to collect from the subject within one heart beat interval magnetic resonance signals (i) to reconstruct an image of each of a plurality of slabs and a magnetic resonance signal (ii) to monitor subject motion in response to a first motion probing pulse (MPP) subsequence and at least one magnetic resonance signal (iii) to display subject motion to the subject in response to at least one second MPP subsequence; and configured to visualize an imaging region containing the plurality of slabs using the collected magnetic resonance signals (i) for reconstruction, the method comprising:
   detecting a first respiratory level of the subject using said magnetic resonance signal (ii) for monitoring;
   controlling the MRI apparatus to collect the magnetic resonance signals (i) for reconstruction when the detected first respiratory level falls within an allowable range that is set with respect to each of the plurality of slabs; and
   setting a single allowable range that is applied to each of the plurality of slabs using respiratory levels detected before the collection of magnetic resonance signals (i) for reconstruction of a first slab in the plurality of slabs to be imaged begins.

8. The method of claim 7, further comprising:
   detecting a second respiratory level using said at least one magnetic resonance signal (iii) for display; and
   displaying said second respiratory level to said subject with respect to said allowable range.

9. A magnetic resonance imaging (MRI) apparatus comprising:
   an MRI gantry having a static magnetic field generator, gradient magnetic field generators and at least one radio-frequency (RF) antenna configured to send RF signals into an image volume and to receive RF signals from said image volume;

an RF signal transmitter and an RF signal receiver coupled to said at least one RF antenna;

a visual display viewable by a patient; and a computer system connected to control said gradient magnetic field generators, said RF signal transmitter and said RF receiver to collect from the patient within one heart beat interval
- (a) magnetic resonance signals (1) to reconstruct at least one slab from patient anatomy located within said image volume using phase encoding magnetic gradient fields, and
- (b) a magnetic resonance signal (2) to monitor patient motion in response to a first motion probing pulse (MPP) subsequence and at least one magnetic resonance signal (3) to display patient motion to the patient in response to at least one second MPP subsequence, without using phase encoding magnetic gradient fields;

wherein said computer system is configured with at least one executable computer program effective, when executed by at least one processor:
- (i) to detect (A) a first respiratory level using said magnetic resonance signal (2) for monitoring, and (B) a second respiratory level from said at least one magnetic resonance signal (3) for display,
- (ii) to generate a visual display to be viewed by said patient using said second respiratory level, and
- (iii) to collect said magnetic resonance signals (1) for reconstruction of a plurality of slabs only when said first respiratory level is within a single acceptable range having upper and lower limits set using respiratory levels detected before collection of magnetic resonance signals (1) for reconstruction begins for the first slab to be imaged of said plurality of slabs.

10. The magnetic resonance imaging apparatus according to claim 9, further comprising a display configured to inform the subject whether the detected second respiratory level falls within the allowable range including visual depiction of said upper and lower limits.

11. The magnetic resonance imaging apparatus according to claim 9, wherein said computer system is further configured to correct the collected magnetic resonance signals (1) for reconstruction to reduce an influence of a fluctuation in the respiratory level.

12. The magnetic resonance imaging apparatus according to claim 11, wherein the display comprises:

first components which are disposed in a second room different from a magnetically shielded first room where other components used to collect the magnetic resonance signals are disposed and which first components are configured to generate an image indicating whether the detected second respiratory level falls within the allowable range;

second components configured to optically transmit the image from the second room to the first room; and a display screen which is disposed in the first room and configured to display the transmitted image to the subject.

13. The magnetic resonance imaging apparatus according to claim 12, wherein:

the first components are configured to generate image information, the second components are configured to transmit the image information by using an optical signal, and the display screen is configured to reproduce and display the image based on the image information.

14. The magnetic resonance imaging apparatus according to claim 12, wherein:

the first components are configured to generate the image as a visible light image, the second components are configured to transmit the visible light image, and the display screen is configured to project the visible light image to eyes of the subject.

* * * * *